United States Patent
Hirayama et al.

(10) Patent No.: US 11,490,276 B2
(45) Date of Patent: *Nov. 1, 2022

(54) COMMUNICATION CONTROL DEVICE, COMMUNICATION CONTROL METHOD, PROGRAM, AND COMMUNICATION CONTROL SYSTEM

(71) Applicant: Sony Corporation, Tokyo (JP)

(72) Inventors: Tomoyuki Hirayama, Kanagawa (JP); Hiroshi Ichiki, Kanagawa (JP); Masahito Yamane, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/016,386

(22) Filed: Sep. 10, 2020

(65) Prior Publication Data

US 2020/0413272 A1 Dec. 31, 2020

Related U.S. Application Data

(63) Continuation of application No. 16/439,702, filed on Jun. 13, 2019, now Pat. No. 10,798,595, which is a
(Continued)

(30) Foreign Application Priority Data

Nov. 7, 2014 (JP) .............................. JP2014-227280

(51) Int. Cl.
*H04W 24/04* (2009.01)
*A61B 1/04* (2006.01)
(Continued)

(52) U.S. Cl.
CPC ......... *H04W 24/04* (2013.01); *A61B 1/00016* (2013.01); *A61B 1/04* (2013.01);
(Continued)

(58) Field of Classification Search
CPC . H04W 24/04; H04W 72/0453; H04W 40/14; H04W 40/34; H04W 80/06;
(Continued)

(56) References Cited

U.S. PATENT DOCUMENTS

| 7,164,932 B1 | 1/2007 | Sato et al. |
| 2008/0019289 A1 | 1/2008 | Monden et al. |

(Continued)

FOREIGN PATENT DOCUMENTS

| EP | 2478823 A1 | 7/2012 |
| JP | 6-69862 A | 3/1994 |

(Continued)

OTHER PUBLICATIONS

Japanese Office Action dated Jun. 11, 2019, issued in corresponding Japanese Patent Application No. 2016-557491.
(Continued)

*Primary Examiner* — Eugene Yun
(74) *Attorney, Agent, or Firm* — Xsensus LLP

(57) ABSTRACT

[Object] To make it possible to more stably perform communication.
[Solution] There is provided a communication control device including: a communication status grasping unit configured to grasp a communication status of wireless communication of image information between an image shooting device and a surgical site image information acquiring unit on the basis of an operating room image showing a situation of an operating room, the image shooting device capturing an image of a surgical site of a patient, the surgical site image information acquiring unit acquiring information on a surgical site image captured by the image shooting device for display control of the surgical site image; and a communication method deciding unit configured to decide a communication method between the image
(Continued)

shooting device and the surgical site image information acquiring unit on the basis of the grasped communication status.

17 Claims, 8 Drawing Sheets

Related U.S. Application Data continuation of application No. 15/522,468, filed as application No. PCT/JP2015/077463 on Sep. 29, 2015, now Pat. No. 10,368,257.

(51) Int. Cl.
| | |
|---|---|
| *H04N 7/18* | (2006.01) |
| *H04W 40/14* | (2009.01) |
| *H04W 40/34* | (2009.01) |
| *H04W 80/06* | (2009.01) |
| *H04W 84/18* | (2009.01) |
| *A61B 1/00* | (2006.01) |
| *H04N 5/232* | (2006.01) |
| *H04W 72/04* | (2009.01) |
| *H04N 5/225* | (2006.01) |

(52) U.S. Cl.
CPC ........... *H04N 5/23206* (2013.01); *H04N 7/18* (2013.01); *H04W 40/14* (2013.01); *H04W 40/34* (2013.01); *H04W 72/0453* (2013.01); *H04W 80/06* (2013.01); *H04W 84/18* (2013.01); *H04N 2005/2255* (2013.01)

(58) Field of Classification Search
CPC ................ H04W 84/18; H04W 40/205; A61B 1/00016; A61B 1/04; H04N 5/23206; H04N 7/18; H04N 2005/2255; H04N 7/183
See application file for complete search history.

(56) References Cited

U.S. PATENT DOCUMENTS

| | | | |
|---|---|---|---|
| 2009/0003251 A1 | 1/2009 | Imae | |
| 2011/0161112 A1 | 6/2011 | Keefe et al. | |
| 2012/0202433 A1 | 8/2012 | Hasegawa et al. | |
| 2013/0063623 A1* | 3/2013 | Kawaguchi | H04N 9/04557 |
| | | | 348/224.1 |
| 2013/0317347 A1 | 11/2013 | Kwiat | |
| 2014/0276056 A1 | 9/2014 | Ohta et al. | |
| 2017/0086199 A1* | 3/2017 | Zhang | H04W 64/00 |

FOREIGN PATENT DOCUMENTS

| | | |
|---|---|---|
| JP | 2009-231996 A | 10/2009 |
| JP | 2010-10759 A | 1/2010 |
| JP | 2010-114774 A | 5/2010 |
| JP | 2011-211662 A | 10/2011 |
| JP | 2011-239223 A | 11/2011 |
| JP | 2013-197887 A | 9/2013 |
| JP | 2014-22999 A | 2/2014 |
| WO | 2011/048914 A1 | 4/2011 |
| WO | 2013/081041 A1 | 6/2013 |
| WO | 2013/081042 A1 | 6/2013 |
| WO | 2015/118733 A1 | 8/2015 |

OTHER PUBLICATIONS

International Search Report dated Dec. 22, 2015 in PCT/JP2015/077463.

\* cited by examiner

COMMUNICATION CONTROL DEVICE, COMMUNICATION CONTROL METHOD, PROGRAM, AND COMMUNICATION CONTROL SYSTEM

CROSS-REFERENCE TO RELATED APPLICATIONS

This application is a continuation of U.S. application Ser. No. 16/439,702, filed Jun. 13, 2019, which is a continuation of U.S. application Ser. No. 15/522,468, filed Apr. 27, 2017 (now U.S. Pat. No. 10,368,257), which is based on PCT filing PCT/JP2015/077463, filed Sep. 29, 2015, and claims priority to JP 2014-227280, filed Nov. 7, 2014, the entire contents of each are incorporated herein by reference.

TECHNICAL FIELD

The present disclosure relates to a communication control device, a communication control method, a program, and a communication control system.

BACKGROUND ART

There is a widely used system that uses an image shooting device such as an endoscope or a microscope to capture an image of a surgical site of a patient, and allows a surgeon to perform an operation while observing the captured image of the surgical site. The system transmits information on the image captured by the image shooting device to a processor (video processor) that performs display control of the image, and causes the video processor to display the image on a display device such as a monitor in an operating room.

The image shooting device and the video processor being for medical use, the situation has to be avoided in which the communication becomes unstable between the image shooting device and the video processor, and the image is distorted during an operation. This is because a serious accident can happen if a distorted image or a disrupted image causes an operation to stop. Stronger stability is therefore requested of the communication between the image shooting device and the video processor in an operating room.

For example, there is proposed a system that connects an endoscope to a video processor through wireless communication. As a method for more stably performing communication between the endoscope and the video processor in the system, it is possible to devise the disposition of the transmitting antenna in the endoscope. There, however, are a large number of people and objects such as a medical staff and medical devices in an operating room. If these people and objects enter the communication path between the endoscope and the video processor, the radio waves can be blocked and the normal communication can be interrupted between the endoscope and the video processor. Even if the disposition of the transmitting antenna is devised in the endoscope, it is difficult to completely prevent such people and objects in the operating room from blocking the communication. The stable communication is not always ensured.

Meanwhile, although not for medical use, the technique described, for example, in Patent Literature 1 is proposed as a technique of more generally strengthening the communication stability of wireless communication. Patent Literature 1 discloses the technique that in a system in which, in a case where a mobile station detects interference information greater than or equal to predetermined reception electric field intensity, a call channel switching request is transmitted to a wireless base station, and the wireless base station transmits an instruction of a new call channel to the mobile station in response to the switching request, the switching request and the instruction of the new call channel are transmitted and received in another frequency band different from that of the call channel. Applying the technique to the communication between the image shooting device and the video processor in an operating room can make the communication more stable.

CITATION LIST

Patent Literature

Patent Literature 1: JP H6-69862A

DISCLOSURE OF INVENTION

Technical Problem

As described above, the image shooting device and the video processor being for medical use, it is unacceptable that the communication becomes unstable between the image shooting device and the video processor, and the image is distorted during an operation. The technique of switching a channel after detecting interference information greater than or equal to predetermined reception electric field intensity, namely detecting that communication is unstable like the technique described in Patent Literature 1 cannot be, however, considered a technique suitable for medical use because a channel is switched after an image is distorted, or the like.

The present disclosure then proposes a novel and improved communication control device, communication control method, program, and communication control system that can more stably perform communication.

Solution to Problem

According to the present disclosure, there is provided a communication control device including: a communication status grasping unit configured to grasp a communication status of wireless communication of image information between an image shooting device and a surgical site image information acquiring unit on the basis of an operating room image showing a situation of an operating room, the image shooting device capturing an image of a surgical site of a patient, the surgical site image information acquiring unit acquiring information on a surgical site image captured by the image shooting device for display control of the surgical site image; and a communication method deciding unit configured to decide a communication method between the image shooting device and the surgical site image information acquiring unit on the basis of the grasped communication status.

Further, according to the present disclosure, there is provided a communication control method including, by a processor: grasping a communication status of wireless communication of image information between an image shooting device and a surgical site image information acquiring unit on the basis of an operating room image showing a situation of an operating room, the image shooting device capturing an image of a surgical site of a patient, the surgical site image information acquiring unit acquiring information on a surgical site image captured by the image shooting device for display control of the surgical site image; and deciding a communication method between the image shooting device and the surgical site image information acquiring unit on the basis of the grasped communication status.

Further, according to the present disclosure, there is provided a program for causing a processor of a computer to execute: a function of grasping a communication status of wireless communication of image information between an image shooting device and a surgical site image information acquiring unit on the basis of an operating room image showing a situation of an operating room, the image shooting device capturing an image of a surgical site of a patient, the surgical site image information acquiring unit acquiring information on a surgical site image captured by the image shooting device for display control of the surgical site image; and a function of deciding a communication method between the image shooting device and the surgical site image information acquiring unit on the basis of the grasped communication status.

Further, according to the present disclosure, there is provided a communication control system including: an operating room camera configured to capture an operating room image showing a situation of an operating room; an image shooting device configured to capture an image of a surgical site of a patient; and a communication control device including a surgical site image information acquiring unit configured to acquire information on a surgical site image captured by the image shooting device for display control of the surgical site image, a communication status grasping unit configured to grasp a communication status of wireless communication of image information between the image shooting device and the surgical site image information acquiring unit on the basis of the operating room image, and a communication method deciding unit configured to decide a communication method between the image shooting device and the surgical site image information acquiring unit on the basis of the grasped communication status.

According to the present disclosure, the communication status of the wireless communication of image information is grasped, on the basis of an operating room image showing the situation of an operating room, between an image shooting device that captures an image of a surgical site of a patient and a display control device that performs display control of a surgical site image captured by the image shooting device. A communication method between the image shooting device and the display control device is then decided on the basis of the grasped communication status. It is thus possible to more stably perform communication between the image shooting device and the display control device.

Advantageous Effects of Invention

As described above, according to the present disclosure, it is possible to more stably perform communication. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is a functional block diagram illustrating an example of a functional configuration of the communication control system according to the first embodiment.

MODE(S) FOR CARRYING OUT THE INVENTION

Figure 1:
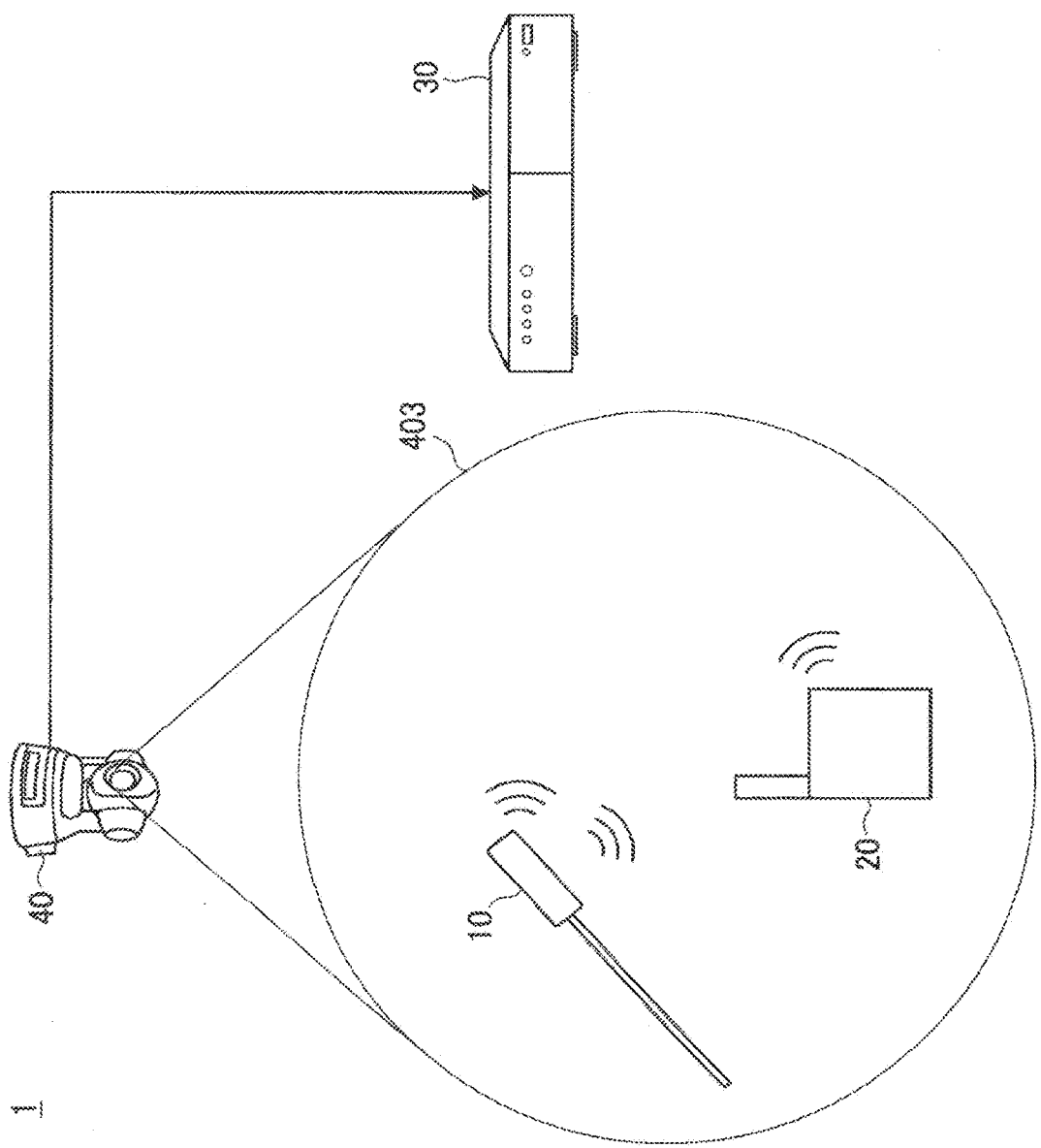
FIG. 1 is a diagram illustrating a schematic configuration of a communication control system according to a first embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be now made in the following order.
1. Consideration of General Technique
2. First Embodiment
2-1. Configuration of Communication Control System
2-2. Functional Configuration of Communication Control System
2-3. Details of Communication Status Grasping Process
2-4. Communication Control Method
3. Second Embodiment
3-1. Details of Communication Status Grasping Process
3-2. Communication Control Method
4. Modifications
4-1. Modification of Decision Process of Communication Method
4-2. Modification of Position for Disposing Operating Room Camera
4-3. Notification of Communication Path
5. Supplemental Information

1. CONSIDERATION OF GENERAL TECHNIQUE

Before an embodiment of the present disclosure is described, a result of the present inventors' consideration of the existing general technique will be described. In addition, the background of the present inventors conceiving of the present disclosure will be described.

As described above, there is a widely used system that uses an image shooting device such as an endoscope or a microscope to capture an image of a surgical site of a patient, and allows a surgeon to perform an operation while watching the captured image of the surgical site (surgical site image). The system transmits image information (surgical site image information) on a surgical site from the image shooting device to a video processor, and causes the video processor to display the surgical site image on a display device such as a monitor in an operating room.

Generally, the image shooting device and the video processor communicate with each other through wired communication in many cases. However, in a case where wired communication is used, the image shooting device in a clean area is connected to the video processor in an unclean area by a cable or the like. Accordingly, more attention has to be paid to maintain the clean area. Further, a heavy load is imposed to sterilize the cable. Moreover, the installation of the cable on the floor can interfere with a medical staff moving in the operating room. Further, there is a concern that the presence of the cable imposes a heavier load on a doctor who operates the image shooting device. Moreover, the cable can interfere with the field of view of a surgeon watching the display device.

There is then a technique developed that connects the image shooting device to the video processor through wireless communication. The image shooting device and the video processor being for medical use, it is unacceptable that the communication becomes unstable between the image shooting device and the video processor during an operation, and the image is distorted. The communication between the image shooting device and the video processor is thus required to be more stable.

The operating room is, however, dotted with a large medical staff, a variety of medical devices, deployment tables (Mayo tables) on which instruments used for operations are placed, and the like. Further, these people and objects can move and be moved during an operation, and the positions thereof are not fixed. For example, if these people and objects enter a communication path between the image shooting device and the video processor, the transmission and reception of the radio waves can be interrupted between the image shooting device and the video processor, and it can be impossible to stably display the image.

Meanwhile, although not for medical use, the technique described, for example, in Patent Literature 1 is disclosed from the perspective of more generally strengthening the communication stability of wireless communication. The technique described in Patent Literature 1 supports, as it were, a technique of selecting a communication path that allows for more stable communication from communication paths. The present inventors have considered a case where the technique described in Patent Literature 1 is applied to the communication between the image shooting device and the video processor in an operating room.

The technique described in Patent Literature 1 targets not relatively small space such as an operating room, but more wide space such as switching wireless base stations for mobile phones. Thus, the technique as described is not always applied to communication in an operating room. Further, as described above, the image shooting device and the video processor being for medical use, the situation has to be avoided in which the communication becomes unstable between the image shooting device and the video processor, and the image is distorted during an operation. The technique of detecting unstable communication, and then switching communication path like the technique Patent Literature 1 is not suitable for medical use from this point of view.

As another method of switching communication paths to make communication more stable, it is possible to conceive of a method that, in a case where, for example, the video processor includes receiving antennas, monitors the reception strength of the communicating receiving antennas and the quality of the received radio waves, thereby switching communication paths to use more stable receiving antennas. The method cannot, however, avoid the distortion or blocking of a surgical site image like the technique described in Patent Literature 1 because communication paths are switched after the reception strength or the quality of the received radio waves decreases.

Here, the recent improvement of the performance of image sensors and the image processing techniques has allowed a surgical site image captured by the image shooting device to have higher resolution. The higher resolution of a surgical site image increases the amount of communication data from the image shooting device to the video processor. Faster communication is required between the image shooting device and the video processor. It is then conceivable to perform communication by using radio waves of, for example, a relatively high frequency band of some 60 (GHz), which is referred to as millimeter waves.

The use of high frequency bands for wireless communication allows for faster information transfer. Radio waves of a high frequency band, however, have the strong property of traveling straight. Accordingly, if there is an obstacle that blocks the radio waves in a communication path between the image shooting device and the video processor, there is a high probability that the communication breaks off. In this way, the higher resolution of a surgical site image in recent years has caused an obstacle in a communication path to have greater influence on the communication.

It is possible to reduce the amount of communication data from the image shooting device to the video processor, for example, by compressing and then transmitting a surgical site image. The use of the method allows for communication with radio waves of a lower frequency band, resulting in a weaker possibility that the above-described obstacle in the communication path interferes with the communication.

The compression of a surgical site image can, however, cause a decrease in the quality of the image or delay in display. Since a surgeon administers various kinds of treatment while watching the surgical site image displayed on the display device, such a decrease in the quality of the image or delay in display can interrupt the surgeon smoothly performing an operation. The method of compressing a surgical site image, and then transmitting the surgical site image is not therefore favorable for medical use because the method can cause a decrease in the quality of the image or delay in display. Although the technique can be found that compresses image information with less delay, such a compression process requires a relatively high-performance processor. The processor and a component such as a battery for driving the processor therefore have to be provided in the image shooting device. The image shooting device can be thus bigger, resulting in the less operability of a medical staff operating the image shooting device.

The result of the present inventors' consideration of the existing general technique has been described above. As described above, it is preferable that the image shooting device wirelessly communicate with the video processor in an operating room because of the inconvenience of the presence of a cable. There are, however, a large number of people and objects in the operating room. These people and objects can serve as obstacles on a communication path between the image shooting device and the video processor, and it can be impossible to perform stable communication. The higher resolution of a surgical site image in recent years especially develops the demand for wireless communication that uses radio waves of high frequency bands, which have the stronger property of traveling straight. There is no ignoring the influence of such obstacles on the communication.

Being for medical use, which does not permit an image that is distorted or breaks off, the method for detecting unstable communication, and then switching the communication path to a more stable communication path, for example, like the technique described in Patent Literature 1 does not sufficiently secure stable communication.

In view of the above-described consideration, the communication of image information in an operating room is particularly required to be more stable because of medical use. It seems difficult for the existing technique to achieve this strong stability. The present inventors diligently studied the technique of allowing for more stable communication on the basis of the above-described result of the consideration of the existing technique. As a result, the present inventors have conceived of the following embodiment of the present disclosure. The following describes, in detail, a preferred embodiment of the present disclosure of which the present inventors have conceived.

2. FIRST EMBODIMENT

A first embodiment of the present disclosure will be described. Additionally, the following describes, as examples of the first embodiment and the following second embodiment, a case where the image shooting device that captures an image of a surgical site of a patient is an endoscope. The present embodiment is not, however, limited to the example. The image shooting device may be another device such as a microscope (operating microscope) for capturing an image of a surgical site.

2-1. CONFIGURATION OF COMMUNICATION CONTROL SYSTEM

The configuration of a communication control system according to the first embodiment of the present disclosure will be described with reference to FIG. 1. FIG. 1 is a diagram illustrating the schematic configuration of the communication control system according to the first embodiment of the present disclosure.

FIG. 1 illustrates that a communication control system 1 according to the first embodiment includes an endoscope 10, at least one relay 20, a video processor 30, and an operating room camera 40.

The endoscope 10 is an example of an image shooting device that captures an image of a surgical site of a patient. The endoscope 10 has a function of wirelessly transmitting image information. The endoscope 10 transmits information on the captured surgical site image to the video processor 30. Although not illustrated, the endoscope 10 includes an antenna for transmitting the surgical site image information. The video processor 30 displays the surgical site image on a display device (not illustrated) such as a monitor provided in an operating room. While watching the surgical site image displayed on the display device, a surgeon performs various kinds of treatment on the surgical site.

The relay 20 has a function of wirelessly transmitting and receiving the surgical site image information. The relay 20 relays the communication between the endoscope 10 and the video processor 30. In the first embodiment, the surgical site image information may be directly transmitted from the endoscope 10 to the video processor 30, or transmitted from the endoscope 10 to the video processor 30 via any of the relays 20. FIG. 1 illustrates only one of the relays 20 for the sake of simplicity, but some of the relays 20 may be installed in fact. Communication paths may be accordingly established.

In the first embodiment, for example, the radio waves referred to as millimeter waves of a frequency band of some 60 (GHz) are used for the communication between the endoscope 10, the relay 20, and the video processor 30. The use of millimeter waves allows for faster communication. Accordingly, for example, in a case where the endoscope 10 can capture a surgical site image having high resolution, the surgical site image information can be transmitted with almost no delay.

A variety of known communication standards may be used for the standard of wireless communication that uses millimeter waves. For example, WirelessHD (registered trademark) or the like can be used for wireless communication for transferring image information with millimeter waves. Further, not limited to the transfer use of image information, for example, what complies with a standard such as IEEE 802.11ad, WiGig (registered trademark), or TGad (registered trademark) may be used for wireless communication that uses millimeter waves.

The first embodiment is not, however, limited to the example. Wireless communication of other frequency bands may be used for the communication between the endoscope 10, the relay 20, and the video processor 30. Embodiments in which wireless communication of these other frequency bands is used will be described again below in (4-1. Modification of Decision Process of Communication Method) in detail.

Additionally, a communication path means a path for transmitting surgical site image information between the endoscope 10 and the video processor 30 in the first embodiment and the following second embodiment. In a case where only one of the relays 20 is provided as illustrated in FIG. 1, there are two communication paths: a communication path for directly transmitting surgical site image information from the endoscope 10 to the video processor 30; and a communication path for transmitting surgical site image information from the endoscope 10 to the video processor 30 via the relay 20.

Further, a communication path also means space through which the radio waves of surgical site image information actually pass in the first and second embodiments. In a case where millimeter waves are used for the communication between the endoscope 10, the relay 20, and the video processor 30 as described above, the communication paths can be created in the substantially straight area that connects the antennas of the communicating devices. This is because radio waves of high frequency bands such as millimeter waves are known to have the strong property of traveling straight.

The operating room camera 40 captures an operating room image showing the situation of an operating room. FIG. 1 schematically illustrates an image capturing range 403 of the operating room camera 40. As illustrated in FIG. 1, the operating room camera 40 is installed to include the antenna of the endoscope 10 and the antenna of the relay 20 at least within the image capturing range 403. For example, the operating room camera 40 is favorably installed on the ceiling of the operating room to look down on the operating room. Information (operating room image information) on the operating room image captured by the operating room camera 40 is transmitted to the video processor 30.

Additionally, the video processor 30 performs wired communication with the operating room camera 40. The video processor 30 and the operating room camera 40 can be both installed in unclean areas. Even if the video processor 30 is connected to the operating room camera 40 by a cable, the presence of the cable does not require so many workloads to maintain clean areas. Further, the operating room camera 40 is installed at a high position such as the ceiling of the operating room. Accordingly, the cable is less likely to interfere with the movement of a medical staff or the like than a cable laid on the floor. The first embodiment is not, however, limited to the example. The video processor 30 may also wirelessly communicate with the operating room camera 40.

The video processor 30 is an example of a display control device that performs control to display a surgical site image captured by the endoscope 10 on the display device. Although not illustrated, the video processor 30 includes an antenna for receiving the surgical site image information. The video processor 30 includes a variety of processing circuits such as a central processing unit (CPU), a digital signal processor (DSP), and a graphics processing unit (GPU). These processing circuits operate in accordance with predetermined programs to realize the functions of the video processor.

The video processor 30 may have a variety of functions of a general display control device. For example, the video processor 30 may have a function of performing general image processing on image information such as adjusting brightness and luminance. The video processor 30 may also perform various kinds of image processing on surgical site image information transmitted from the endoscope 10, and then display the surgical site image on the display device.

Further, the video processor 30 controls the communication of surgical site image information in the communication control system 1 in the first embodiment. Specifically, the video processor 30 grasps the communication status between the endoscope 10 and the video processor 30 itself on the basis of an operating room image captured by the operating room camera 40. The video processor 30 then decides a communication method between the endoscope 10 and the video processor on the basis of the grasped communication status. In this way, the video processor 30 is a display control device, and also functions as a communication control device. Additionally, the detailed functions of the video processor 30 will be described again below in (2-2. Functional Configuration of Communication Control System).

Figure 2:
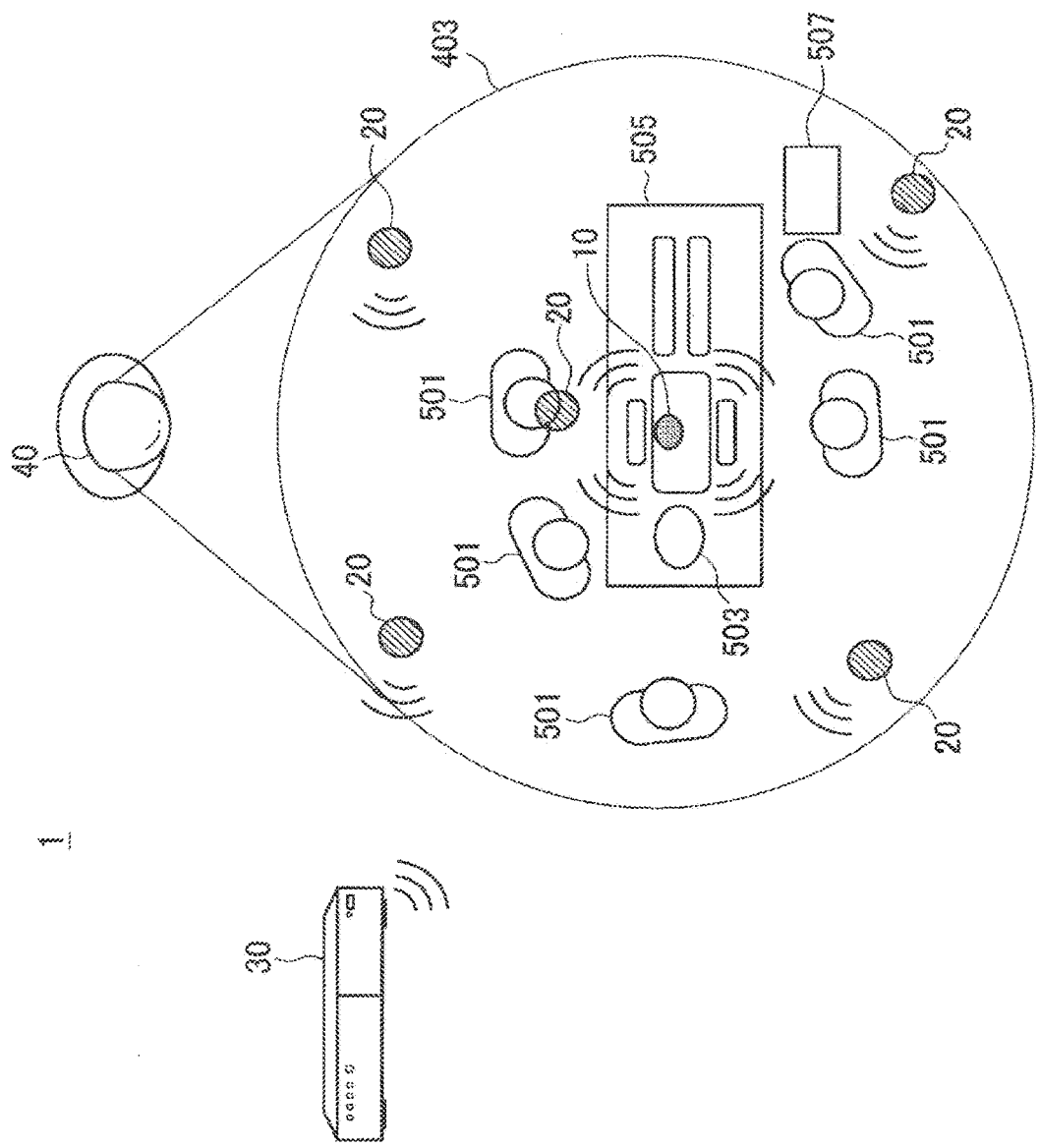
FIG. 2 is a diagram illustrating a more detailed configuration of the communication control system according to the first embodiment.

Here, the configuration of the communication control system 1 according to the first embodiment will be described in more detail with reference to FIG. 2. FIG. 2 is a diagram illustrating the more detailed configuration of the communication control system 1 according to the first embodiment. FIG. 2 illustrates an overhead view of a configuration example of the communication control system 1 illustrated in FIG. 1 and actually installed in an operating room.

FIG. 2 illustrates that a patient 503 lies down on an operating table 505. The operating table 505 is surrounded by a medical staff 501 such as doctors and nurses. The place of the medical staff 501 move as needed during an operation.

The operating table 505 is further surrounded by other objects such as a Mayo table 507 on which surgical instruments are placed. Further, although not illustrated, the operating table 505 can be surrounded by a variety of medical devices such as a measurement device used for an operation to measure the vital signs of a patient. The places of the Mayo table 507 and these medical devices can also be moved as needed during an operation.

Objects such as the medical staff 501 and the Mayo table 507 can block the radio waves between the endoscope 10 and the video processor 30 in an operating room, and obstruct the communication. The following also refers to objects such as the medical staff 501 and the Mayo table 507 that can obstruct the communication as obstacles in a case where the objects have to be distinguished from other objects.

The lens barrel of the endoscope 10 is inserted into a body cavity of the patient 503, and the endoscope 10 captures an image of a surgical site in the body cavity in an endoscopic operation. The endoscope 10 is held by a medical specialist referred to as scopist during an operation.

The relays 20 are disposed at different positions in an operating room. In the illustrated example, the four relays 20 are disposed around the operating table 505, and the one relay 20 is also disposed on the head of the scopist. The positions of the four relays 20 provided around the operating table 505 are, for example, fixed Meanwhile, needless to say, the one relay 20 provided on the head of the scopist can move in accordance with the movement of the scopist. In this way, the position for disposing the relay 20 is decided in advance. The relay 20 does not have to change the position during an operation, or may also be disposed in a place such as the head of a member of the medical staff 501 that can move during an operation.

The positions for disposing the relays 20 and the number of relays 20 to be disposed are not limited to the example. Any number of relays 20 may be disposed at any positions. For example, any number of relays 20 may be disposed at any positions such as the operating table 505, the ceiling of the operating room, or the body of another member of the medical staff. In a case where the relay 20 is disposed at a relatively high position such as the ceiling or the head of a member of the medical staff 501, another object is less likely to interfere with the relay 20 transmitting and receiving radio waves. Accordingly, it is possible to further enhance the stability of the communication path via the relay 20.

A surgical site image captured by the endoscope 10 is transmitted to the video processor 30 directly or via the relay 20. The video processor 30 displays the surgical site image on the display device provided in the operating room. The video processor 30 may be disposed at any position in the operating room. The video processor 30 is, however, disposed at a position at which the video processor 30 can communicate with at least any one of the endoscope 10 or the relay 20.

The operating room camera 40 is disposed to include the antenna of the endoscope 10 and the antennas of the relays 20 at least within in the image capturing range 403. The operating room camera 40 is favorably disposed on the ceiling of the operating room. The operating room camera 40 may be disposed at the position right above the space including the endoscope 10 and the relays 20, or the position obliquely looking down on the space. An operating room image captured by the operating room camera 40 is transmitted to the video processor 30 through wired or wireless communication. The video processor 30 performs a process of controlling the communication of the surgical site image information in the communication control system 1 on the basis of the operating room image.

The configuration of the communication control system 1 according to the first embodiment has been described above with reference to FIGS. 1 and 2.

2-2. FUNCTIONAL CONFIGURATION OF COMMUNICATION CONTROL SYSTEM

Figure 3:
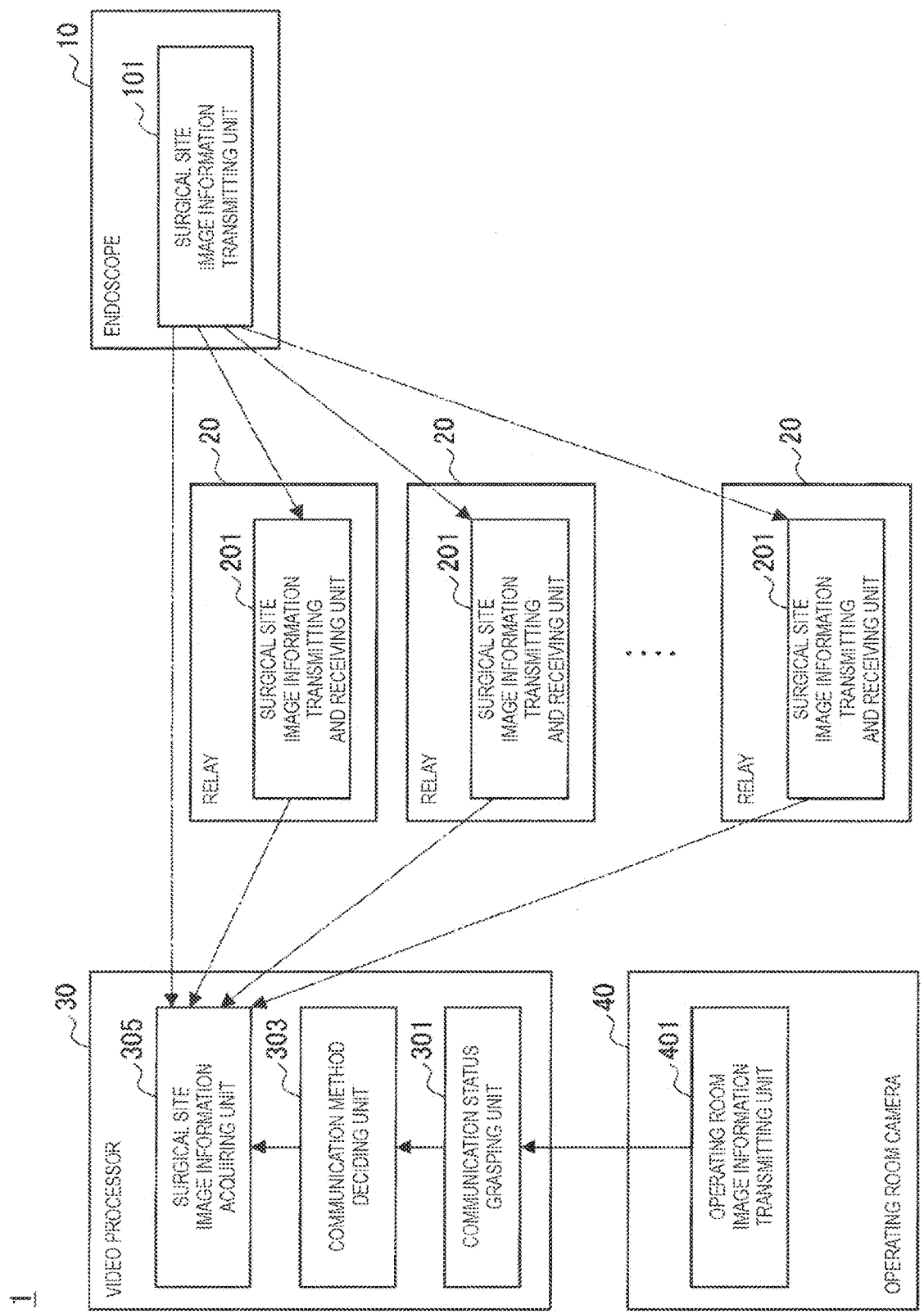
[FIG. 3]

The functional configuration of the communication control system 1 according to the first embodiment will be described with reference to FIG. 3. FIG. 3 is a functional block diagram illustrating an example of the functional configuration of the communication control system 1 according to the first embodiment. FIG. 3 corresponds to the illustration showing the functions of each device in the communication control system 1 illustrated in FIGS. 1 and 2 as functional blocks. Each function illustrated as a functional block is realized by processing circuits such as a CPU, a DSP, and a GPU each provided in the endoscope 10, the relay 20, the video processor 30, and the operating room camera 40 operating in accordance with predetermined programs. Among arrows indicating the transmission and reception of information, FIG. 3 illustrates a one-dot arrow to indicate the transmission and reception of information through wireless communication, and a solid arrow to indicate the transmission and reception of information through wired communication.

FIG. 3 illustrates that the endoscope 10 includes a surgical site image information transmitting unit 101 as a function thereof. The surgical site image information transmitting unit 101 has a function of wirelessly transmitting information on an image of a surgical site of a patient captured by the endoscope 10 to the following surgical site image information acquiring unit 305 of the video processor 30 and the following surgical site image information transmitting and receiving unit 201 of the relay 20 via a transmitting antenna provided to the endoscope 10.

The relay 20 includes the surgical site image information transmitting and receiving unit 201 as a function thereof. The surgical site image information transmitting and receiving unit 201 has a function of wirelessly receiving surgical site image information transmitted from the surgical site image information transmitting unit 101 of the endoscope 10 via a transmitting and receiving antenna provided to the relay 20, and wirelessly transmitting the surgical site image information to the following surgical site image information acquiring unit 305 of the video processor 30.

In the example illustrated in FIG. 3, there are a communication path for directly transmitting surgical site image information from the endoscope 10 to the video processor 30, and a communication path for transmitting surgical site image information from the endoscope 10 to the video processor 30 via any of the relays 20. In this way, the number of communication paths can be decided in accordance with the number of relays 20 to be provided to the communication control system 1. The wireless channels corresponding to the respective communication paths are set for the video processor 30 in advance. The video processor 30 has a function of selecting a communication path for acquiring surgical site image information by switching the wireless channels (i.e., function of selecting through which communication path the radio waves to be used propagate through any of the communication paths).

The operating room camera 40 includes an operating room image information transmitting unit 401 as a function thereof. The operating room image information transmitting unit 401 has a function of transmitting, in a wired manner, information on an operating room image captured by the operating room camera 40 and showing the situation of the operating room to the following communication status grasping unit 301 of the video processor 30. The operating room image includes the antenna of the endoscope 10 and the antennas of the relays 20 disposed in the operating room at least within the image.

The video processor 30 includes the communication status grasping unit 301, a communication method deciding unit 303, and the surgical site image information acquiring unit 305 as functions thereof. The communication status grasping unit 301 grasps the communication status between the endoscope 10 and the video processor 30 on the basis of an operating room image captured by the operating room camera 40. Specifically, the communication status grasping unit 301 grasps the environment of a communication path between the endoscope 10 and the video processor 30, such as the stability of the communication in the communication path, as the communication status.

More specifically, the communication status grasping unit 301 detects the positions of antennas forming the communication path, namely the position of the antenna of the endoscope 10 and the positions of the antenna of the relay 20 which transmit and receive radio waves, on the basis of an operating room image. In a case where the relay 20 can be moved on the head of a member of the medical staff 501 or the like, the communication status grasping unit 301 also detects the position of the moving relay 20 on the basis of the operating room image. A variety of known image analysis techniques that detect a predetermined object from an image can be used for a process of detecting the position of the antenna of the endoscope 10 and the position of the antenna of the relay 20 on the basis of an operating room image. The details will not be thus described.

Here, in the first embodiment, when the video processor 30 is installed, the position information of the antenna of the video processor 30 is input in advance to a storage device (such as a storage device in the video processor 30) that the communication status grasping unit 301 can access. The communication status grasping unit 301 can thus detect a communication path between the endoscope 10 and the video processor 30 on the basis of the position information of the antenna of the video processor 30, and the position of the position of the antenna of the endoscope 10 and the position of the antenna of the relay 20 detected on the basis of an operating room image. For example, the communication status grasping unit 301 detects communication paths as a substantially straight line connecting the antenna of the endoscope 10 to the antenna of the relay 20, a substantially vertical line connecting the antenna of the endoscope 10 to the antenna of the video processor 30, and/or a substantially straight line connecting the antenna of the relay 20 to the antenna of the video processor 30. Additionally, in a case where the endoscope 10, the relay 20, and/or the video processor 30 include antennas, the communication status grasping unit 301 detects or acquires the respective positions of the antennas and detects communication paths for the respective antennas.

In a case where the video processor 30 is included in an operating room image, the communication status grasping unit 301 may acquire position information of the antenna of the video processor 30 by detecting the position of the antenna of the video processor 30 on the basis of the operating room image.

Moreover, the communication status grasping unit 301 detects the position of an object (obstacle) such as the medical staff 501 or the Mayo table 507 in an operating room illustrated in FIG. 2 that can obstruct communication, on the basis of an operating room image. The communication status grasping unit 301 then grasps the communication status of each communication path on the basis of the positional relationship between the communication path and the obstacle in the operating room. For example, in a case where there is an obstacle on a communication path, the communication status grasping unit 301 determines that the stability of the communication in the communication path is weak. Meanwhile, for example, in a case where there is no obstacle on a communication path, the communication status grasping unit 301 determines that the stability of the communication in the communication path is strong.

The communication status grasping unit 301 provides the communication method deciding unit 303 with information on the grasped communication status of each communication path, namely information on the stability of the communication.

The communication method deciding unit 303 decides a communication method between the endoscope 10 and the video processor 30 on the basis of the grasped communication status between the endoscope 10 and the video processor 30 by the communication status grasping unit 301. Specifically, for example, as described above, the communication status between the endoscope 10 and the video processor 30 means the stability of the communication in a communication path between the endoscope 10 and the video processor 30. The communication method deciding unit 303 selects a communication path that allows for more stable communication from communication paths as a communication method on the basis of information on the stability of the communication in each communication path. The communication path that allows for more stable communication means a communication path having no obstacle thereon in other words.

The communication method deciding unit 303 provides information on the selected communication path to the surgical site image information acquiring unit 305.

The surgical site image information acquiring unit 305 switches wireless channels to receive a surgical site image by using the radio waves passing through the communication path selected by the communication method deciding unit 303. The surgical site image information is then acquired from the endoscope 10 by using the radio waves passing through the communication path. The communication path selected by the communication method deciding unit 303 is a communication path that has no obstacle thereon, and allows for stable communication. The surgical site image information acquiring unit 305 can therefore more stably acquire the surgical site image.

The video processor 30 includes a display control unit (not illustrated) as a function thereof. The surgical site image acquired by the surgical site image information acquiring unit 305 is displayed by the display control unit on the display device in an operating room. The surgical site image more stably acquired by the surgical site image information acquiring unit 305 is displayed on the display device. The surgical site image can be hereby displayed on the display device without being distorted or breaking off. It is then possible to prevent a deficient image from interrupting with an operation.

The above-described series of processes performed by the communication status grasping unit 301, the communication method deciding unit 303, and the surgical site image information acquiring unit 305 is repeatedly executed at predetermined intervals. This keeps a more stable communication path selected, and always stably transmits a surgical site image to the video processor 30 through the communication path.

Figure 4:
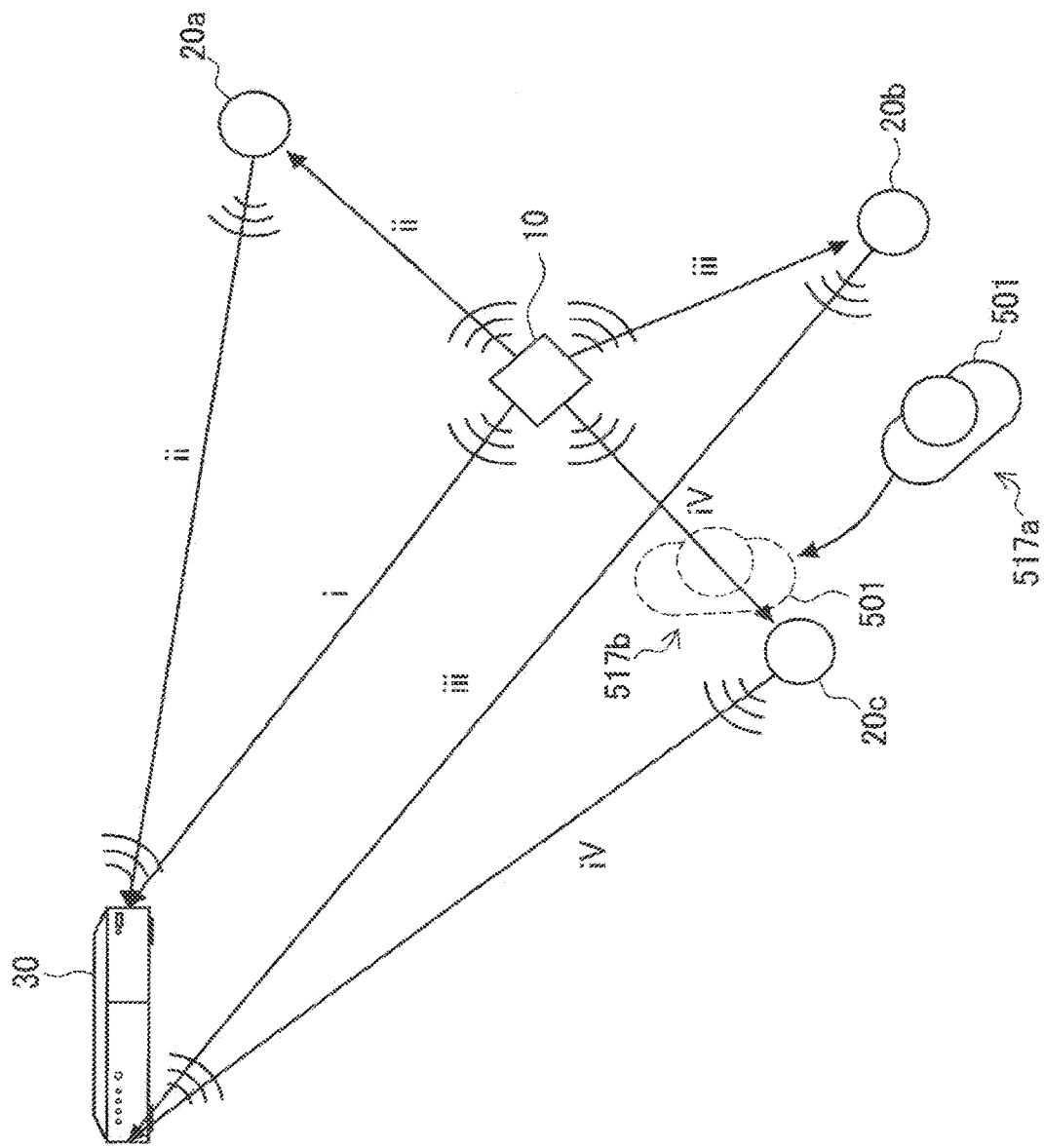
FIG. 4 is an explanatory diagram for describing a function of a video processor illustrated in FIG. 3 in more detail.

Here, the functions (the communication status grasping unit 301, the communication method deciding unit 303, and the surgical site image information acquiring unit 305) of the video processor 30 illustrated in FIG. 3 will be described in more detail with reference to FIG. 4. FIG. 4 is an explanatory diagram for describing a function of the video processor 30 illustrated in FIG. 3 in more detail.

FIG. 4 schematically illustrates the endoscope 10, relays 20a to 20c, and the video processor 30. FIG. 4 also simulatively illustrates communication paths i to iv by solid arrows. Further, the medical staff 501 is illustrated in an operating room.

The communication path i is a communication path directly extending from the endoscope 10 to the video processor 30. The communication path ii is a communication path extending from the endoscope 10 to the video processor 30 via the relay 20a. The communication path iii is a communication path extending from the endoscope 10 to the video processor 30 via the relay 20b. The communication path iv is a communication path extending from the endoscope 10 to the video processor 30 via the relay 20c. As described above, the communication paths i to iv can be schematically represented as substantially straight lines connecting devices (more specifically, the antennas of devices) as simulatively illustrated in FIG. 4 in communication that uses millimeter waves because of the strong property of traveling straight.

The communication status grasping unit 301 illustrated in FIG. 3 detects the position of the antenna of the endoscope 10, the positions of the antennas of the relays 20a to 20c and the position of the medical staff 501 on the basis of an operating room image in the first embodiment. Further, the position of the antenna of the video processor 30 is provided in advance as known information. The communication status grasping unit 301 grasps the communication statuses in communication paths i to iv on the basis of the detected position of the antenna of the endoscope 10, the detected positions of the antennas of the relays 20a to 20c and the detected position of the medical staff 501, and the position of the antenna of the video processor 30, which is provided in advance.

In a case where a member of the medical staff 501 is at a position 517a, there is no obstacle on any of the communication paths i to iv in the example illustrated in FIG. 4. The communication status grasping unit 301 thus determines that the communication status is stable in any of the communication paths i to iv. In this case, the communication method deciding unit 303 illustrated in FIG. 3 can select any communication path from the communication paths i to iv on the basis of a result of the determination made by the communication status grasping unit 301. The surgical site image information acquiring unit 305 illustrated in FIG. 3 then acquires a surgical site image from the endoscope 10 by using the wireless channel corresponding to any communication path selected by the communication method deciding unit 303 from the communication paths i to iv.

Here, it is assumed that the member of the medical staff 501 moves from the position 517a to a position 517b. The position 517b is a position on the communication path iv as illustrated. In this case, the communication status grasping unit 301 illustrated in FIG. 3 detects the new position 517b of the member of the medical staff 501 from the updated and latest operating room image along with the position of the antenna of the endoscope 10 and the positions of the antennas of the relays 20a to 20c. The communication status grasping unit 301 then determines that, among the communication paths i to iv, the communication statuses in communication paths i to iii are stable, but the communication status in the communication path iv is not stable.

The communication method deciding unit 303 illustrated in FIG. 3 selects any communication path from the communication paths i to iii that allow for more stable communication among the communication paths i to iv, on the basis of a result of the determination of the communication status grasping unit 301. The surgical site image information acquiring unit 305 illustrated in FIG. 3 then acquires a surgical site image from the endoscope 10 by using the wireless channel corresponding to any communication path selected by the communication method deciding unit 303 from the communication paths i to iii.

The configuration of the communication control system according to the first embodiment has been described above. As described above, according to the first embodiment, the position of an obstacle in a communication path which can obstruct the communication is detected on the basis of an operating room image, and a communication path that does not have the obstacle therein is selected as the communication path for a surgical site image. It is thus possible to more stably transmit a surgical site image from the endoscope 10 to the video processor 30.

Since more stable wireless communication is realized between the endoscope 10 and the video processor 30 in this way according to the first embodiment, there is no need to perform wired communication between the endoscope 10 and the video processor 30 by using a cable. Cables are dispensable between the endoscope 10 and the video processor 30. It is thus possible to reduce the load on a scopist, securing a surgeon a wider field of view. Further, the efficiency and safety of an operation are accordingly improved. Further, the absence of a cable makes it easier to maintain a clean area, and to reduce the load for sterilizing the cable. Moreover, the movement of the medical staff is not interrupted by the cable laid on the floor. Neither does the endoscope 10 shaken by accidental contact with the cable on the floor cause a surgical site image to blur. Accordingly, the efficiency and safety of an operation are improved.

Here, as a different method from the method according to the present embodiment which grasps the communication status of an operating room, it is possible to conceive of a method that attaches cameras or sensors to a person and an object in the operating room to detect the positions or motion of the person and object, detects the positions of the person and object in the operating room by integrating the position information or motion information detected by those cameras or sensors, and grasps the communication status.

The method, however, requires, as a precondition, that all the objects whose positions to be detected be provided components such as cameras or sensors needed to detect the positions. The number of people or objects in an operating room actually depends on, for example, the types of operation or the like in medical scenes. Further, people or objects can enter or leave an operating room during an operation. It is not realistic from the perspective of increasing costs or complicated preparations to grasp, in advance, all the objects such as a medical staff, medical devices, and Mayo tables that can be in an operating room during an operation, and to install the component such as a camera or sensor to every object.

Meanwhile, as described above, the position of an object in an operating room is detected on the basis of an operating room image, and the communication status is grasped in the present embodiment. The operating room image can be acquired by a relatively simple component such as the one operating room camera 40. There is therefore no need to do large-scale and complicated preparations unlike the above-described method. According to the present embodiment, it is thus possible to grasp the communication status with a simpler component by performing a grasping process based on an operating room image.

The operating room camera 40 is installed to include the antenna of the endoscope 10 and the antennas of the relays 20 within an operating room image in the above-described embodiment. The first embodiment is not, however, limited to the example. For example, the antennas of all the relays 20 do not have to be included within the image shooting range. For example, in a case where the positions of the relays 20 are fixed during an operation, and the positions of the relays 20 in an operating room are known in advance, the position information of the antennas of the relays 20 may be input beforehand similarly to the video processor 30. In this case, the communication status grasping unit 301 of the video processor may detect a communication path on the basis of the positions of the antennas of the relays 20 provided in advance in addition to the position of the antenna of the endoscope 10 and the positions of the antennas of the relays 20 detected on the basis of an operating room image.

Further, a specific device configuration for realizing the communication control system 1 according to the first embodiment is not limited to the example illustrated in FIG. 3. For example, the respective functions of the communication status grasping unit 301, the communication method deciding unit 303, and the surgical site image information acquiring unit 305 of the video processor 30 do not have to be necessarily executed by one device. For example, the video processor 30 merely has the functions of a general display control device alone, and the respective functions corresponding to the communication status grasping unit 301, the communication method deciding unit 303, and the surgical site image information acquiring unit 305 may be executed by another information processing device different from the video processor 30. Alternatively, the respective functions corresponding to the communication status grasping unit 301, the communication method deciding unit 303, and the surgical site image information acquiring unit 305 may be distributed in information processing devices (such as processors), and the devices may be communicably connected to each other and operated in cooperation, thereby realizing the above-described functions of the communication control system 1. The information processing devices may be local information processing devices installed near an operating room, or information processing devices installed remotely from an operating room (what is called cloud computing).

It is possible to create a computer program for realizing the respective functions of the communication control system 1 according to the above-described first embodiment and the following second embodiment, in particular, the respective functions corresponding to the communication status grasping unit 301, the communication method deciding unit 303, and the surgical site image information acquiring unit 305, and to implement the created computer program in a personal computer or the like. Further, there can also be provided a computer-readable recording medium having such a computer program stored therein. The recording medium is, for example, a magnetic disk, an optical disc, a magneto-optical disk, a flash memory, or the like. Further, the above-described computer program may be distributed, for example, via a network without any recording medium.

2-3. DETAILS OF COMMUNICATION STATUS GRASPING PROCESS

Figure 5:
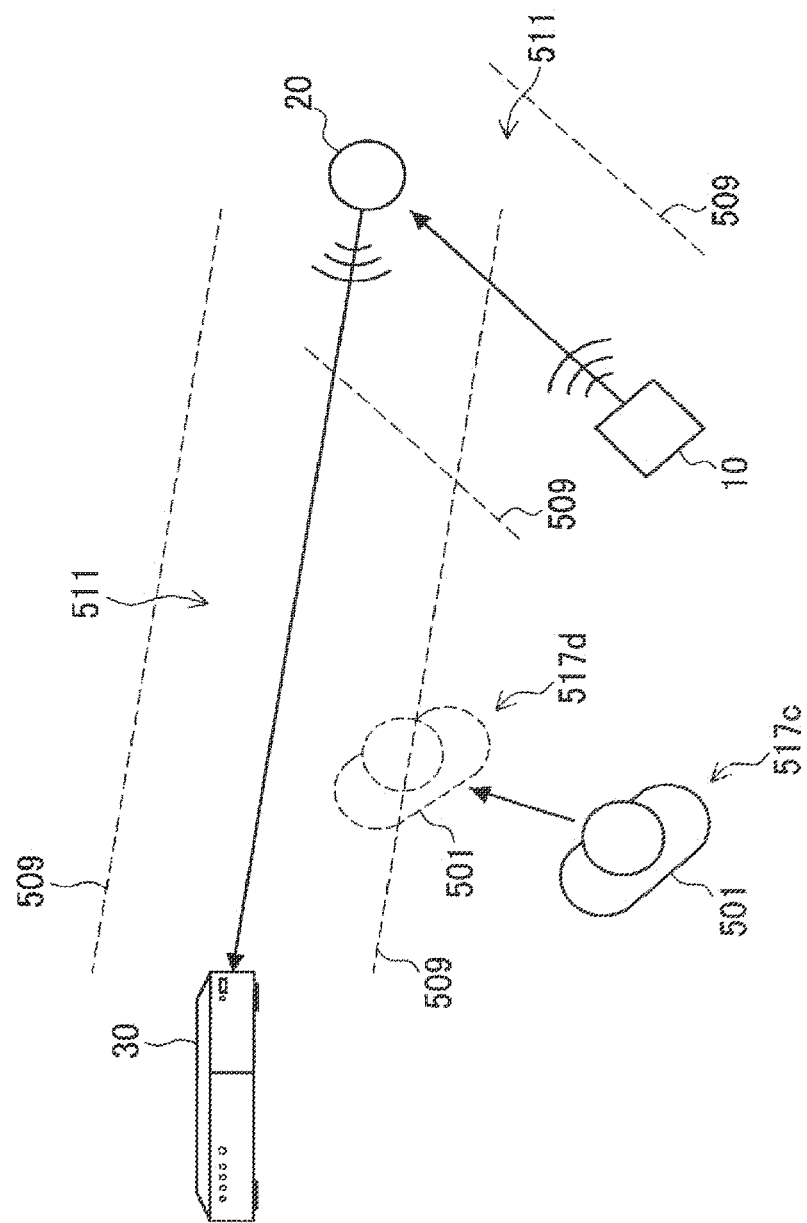
FIG. 5 is an explanatory diagram for describing a communication status grasping process executed by a communication status grasping unit in the first embodiment in more detail.

As described with reference to FIG. 4, the communication status grasping unit 301 illustrated in FIG. 3 grasps the communication status of a communication path in accordance with whether an obstacle is in the communication path. Here, a communication status grasping process executed by the communication status grasping unit 301 in the first embodiment, such as a criterion for determining whether an obstacle is in a communication path, will be described in more detail with reference to FIG. 5. FIG. 5 is an explanatory diagram for describing a communication status grasping process executed by the communication status grasping unit 301 in the first embodiment in more detail.

FIG. 5 schematically illustrates the endoscope 10, the relay 20, and the video processor 30. FIG. 5 simulatively illustrates communication paths from the endoscope 10 to the video processor 30 via the relay 20 by solid arrows. Further, a member of the medical staff 501 is illustrated as an example of an obstacle in an operating room.

As illustrated in FIG. 5, a predetermined area including a communication path is set as alerting areas 511 in the first embodiment. Specifically, the alerting area 511 is set as the areas included in a predetermined distance from a substantially straight line connecting the wireless input and output points (i.e., antennas) of the respective devices on a communication path. In the example illustrated in FIG. 5, the areas included in a predetermined distance from a substantially straight line connecting the antenna of the endoscope 10 to the antenna of the relay 20, and a substantially straight line connecting the antenna of the relay 20 to the antenna of the video processor 30 are set as the alerting areas 511. Additionally, FIG. 5 illustrates alerting lines 509 serving as the borders of the alerting areas 511 by dashed lines. The alerting areas 511 include an area in which the presence of an object can actually block radio waves, and areas larger than the area are set as the alerting areas 511.

The communication status grasping unit 301 detects the position of the antenna of the endoscope 10 and the position of the antenna of the relay 20 on the basis of an operating room image, and detects the position (spatial coordinates) of a communication path in an operating room on the basis of the position information thereof, the position information of the antenna of the video processor 30 input in advance in the first embodiment. The communication status grasping unit 301 then sets the alerting area 511 for the communication path. Further, the communication status grasping unit 301 detects the position (spatial coordinates) of a member of the medical staff 501 in the operating room on the basis of the operating room image.

For example, it is assumed that the member of the medical staff 501 moves from a position 517c to a position 517d. The position 517d is a position at which the body of the member of the medical staff 501 is in the alerting area 511 as illustrated. In this case, the communication status grasping unit 301 illustrated in FIG. 3 detects the new position 517c of the member of the medical staff 501 from the updated and latest operating room image along with the position of the antenna of the endoscope 10 and the position of the antenna of the relay. The communication status grasping unit 301 then detects that the body of the member of the medical staff 501 is in the alerting area 511 at the new position 517d, and determines that the communication status in the communication path is not stable. The communication method deciding unit 303 illustrated in FIG. 3 switches the wireless channel to another communication path having no object in the alerting area 511 on the basis of a result of the determination made by the communication status grasping unit 301.

In this way, the alerting area 511 is set for a communication path, and the stability of the communication in the communication path is determined in accordance with the entry of an object to the alerting area 511 in the first embodiment. Here, the alerting area 511 is set as the area included in a predetermined distance from a substantially straight line connecting the wireless input and output points of the respective devices on the communication path. Accordingly, an object beginning to enter the alerting area 511 does still not hinder the wireless communication that uses the communication path. That is, the entry of an object to the alerting area 511 does not indicate that the communication in that communication path is actually interrupted, but that the communication in the communication path can be interrupted.

The stability of the communication in the communication path is determined in accordance with the entry of an object to the alerting area 511 in the first embodiment, thereby making it possible to predict that the communication can be interrupted before the object actually interrupt the communication, and to switch the wireless channel to a communication path that allows for more stable communication. In this way, the communication status grasping unit 301 illustrated in FIG. 3 has a function of predicting the risk of interference with communication, and the communication method deciding unit 303 has a function of selecting a more stable communication path having no interference with the communication, on the basis of a result of the prediction. The components make it possible to more stably display a surgical site image that is not distorted than the method executed, for example, as an existing technique for monitoring the strength or the like of radio waves during communication and switching wireless channels. It is thus possible to smoothly perform an operation, and to reduce the load on a patient and a medical staff.

A communication path and the alerting area 511 may be set as appropriate in accordance with the frequency band of radio waves used for wireless communication. The example illustrated in FIG. 5 assumes the use of millimeter waves, which have the stronger property of traveling straight. Accordingly, the alerting areas 511 are set for substantially straight lines connecting the devices on the communication paths. For example, in a case where radio waves of a lower frequency band are used, the radio waves are predicted to diffuse more and propagate between the devices. The alerting areas 511 may be therefore set, for example, as substantially conical areas that gradually increase in cross-sectional area from the antenna of the transmitting device to the antenna of the receiving device. In this way, in light of the frequency band or the like of radio waves used for wireless communication, the alerting areas 511 can be set as areas that include an area in which the presence of an object can actually block the radio waves, and are larger than the area.

2-4. COMMUNICATION CONTROL METHOD

Figure 6:
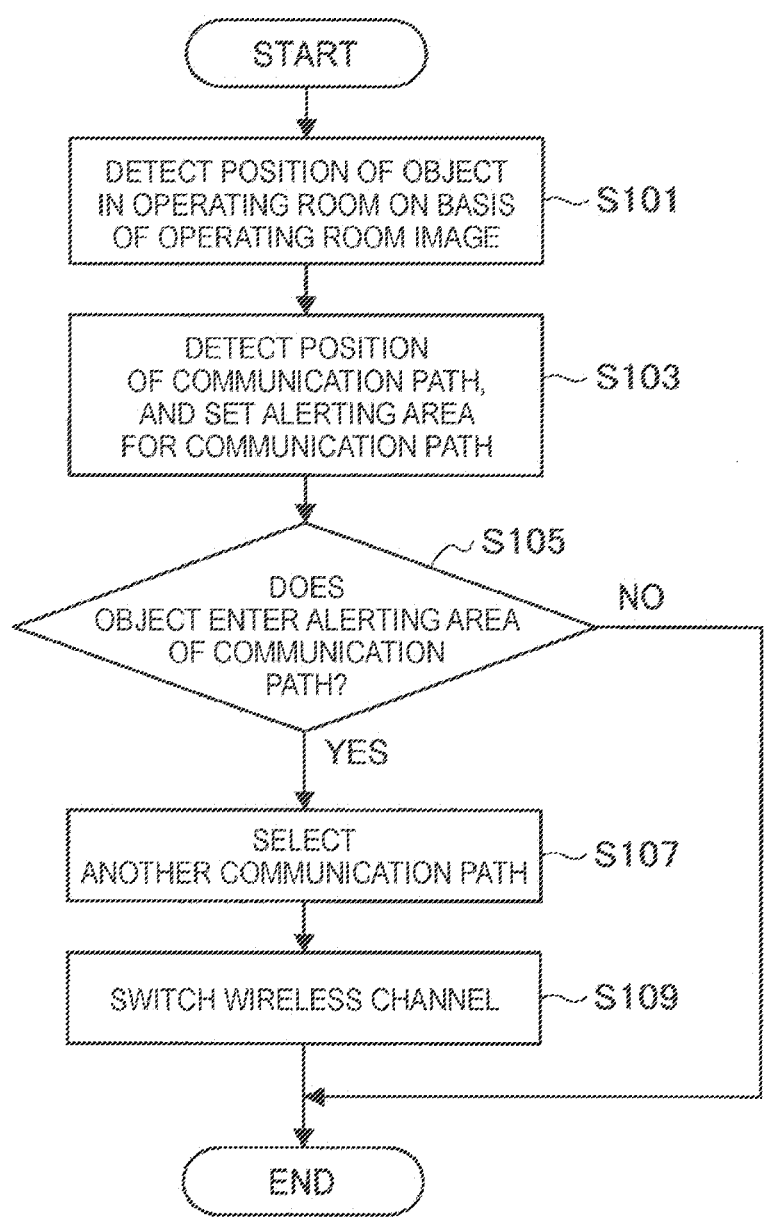
FIG. 6 is a flowchart illustrating an example of a processing procedure of a communication control method according to the first embodiment.

A processing procedure of a communication control method according to the first embodiment will be described with reference to FIG. 6. FIG. 6 is a flowchart illustrating an example of a processing procedure of the communication control method according to the first embodiment.

FIG. 6 illustrates that the position of an object in an operating room is first detected on the basis of an operating room image in the communication control method according to the first embodiment (step S101). Specifically, in step S101, the positions of the wireless input and output points (antennas) of respective devices that transmit surgical site image information from the endoscope 10 to the video processor 30, and the position of an object (such as the medical staff 501 or the Mayo table 507 illustrated in FIG. 2) that can obstruct the communication are at least detected. However, the positions of the antennas of all the devices do not have to be necessarily detected on the basis of the operating room image. The position information of the antennas of some of the devices such as the video processor 30 may also be input in advance as known data.

Next, the position of a communication path is detected on the basis of the position of the object detected in step S101, and an alerting area is set for the detected communication path (step S103). For example, in a case where millimeter waves are used for wireless communication, the communication path is detected as a substantially straight line connecting the antennas of the respective devices that transmit the surgical site image information from the endoscope 10 to the video processor 30, in light of the strong property of the millimeter waves to travel straight. Further, the alerting area is set as the area included in a predetermined distance from the line of the communication path (see FIG. 5).

The first embodiment is not, however, limited to the example. The communication path may be detected on the basis of the positions of the antennas of the respective devices in light of the frequency band or the like of radio waves used for wireless communication. Further, the alerting areas include an area in which the presence of an object can actually block radio waves, and areas larger than the area can be set as the alerting areas 511.

Next, it is determined on the basis of the position of the object detected in step S101 and the alerting area set in step S103 whether the object is in the alerting area of the communication path (step S105).

In a case where it is not determined in step S105 that the object is in the alerting area, the series of processes according to the communication control method ends with no particular processes, and the communication of surgical site image information continues in the communication path. Meanwhile, in a case where it is determined in step S105 that the object is in the alerting area, the processes proceed to step S107.

The processes shown in step S101 to step S105 correspond to, for example, processes performed by the communication status grasping unit 301 illustrated in FIG. 3.

In step S107, another communication path is selected that is different from the communication path having the object in the alerting area. A communication path that has no object in the alerting area and allows for more stable communication is selected as the other communication path from the communication paths detected in step S103. The wireless channel is then switched to the wireless channel corresponding to the communication path selected in step S107 (step S109). This switches the wireless channel from the communication path having the risk that an object enters the alerting area and interrupts the communication to a communication path that allows for more stable communication. It is thus possible to transmit the surgical site image information to the video processor 30 without the surgical site image information breaking off.

The respective processes shown in step S107 and step S109 correspond to, for example, processes performed by the communication method deciding unit 303 illustrated in FIG. 3.

The processing procedure of the communication control method according to the first embodiment has been described above with reference to FIG. 6. The series of processes illustrated in FIG. 6 is repeatedly executed at predetermined intervals in the first embodiment. A stable surgical site image is thus always displayed.

3. SECOND EMBODIMENT

The second embodiment of the present disclosure will be described.

An alerting area is set for a communication path, and the stability of the communication in the communication path is determined in accordance with the entry of an object to the alerting area in the above-described first embodiment. However, for example, in a case where an object that stands still is in an alerting area, but the object is at a position at which the object does not block communication, the communication path can be considered a communication path that allows for stable communication. Meanwhile, even if a moving object in an alerting area is at a position at which the object does not block communication, the communication path should be determined as a communication path that does not allow for stable communication. This is because the influence of the moving object on the communication path temporally depends on the movement thereof, the moving object therefore has greater influence on wireless communication that that of the object that stands still, and in a case where the moving object is in the alerting area, there is a high probability that the stability of the communication is going to be much weaker soon.

Even in a case where the object is in the alerting area of the communication path in this way, the determination of the stability of the communication of the communication path can be different in accordance with whether the object is a still object or a moving object. When an object in an operating room is detected on the basis of an operating room image, it is determined even whether the object is a still object or a moving object, and the communication status of the communication path is determined even in light of the motion of the object in second embodiment. It is thus possible to more accurately grasp the communication status of the communication path.

The second embodiment will be described in more detail. Here, the configuration of a communication control system according to the second embodiment may be similar to the configuration of the communication control system 1 according to the first embodiment illustrated in FIGS. 1 and 2. Further, the functional configuration of the communication control system according to the second embodiment may also be similar to the functional configuration of the communication control system 1 according to the first embodiment illustrated in FIG. 3. The second embodiment is different from the first embodiment in the detailed functions of the communication status grasping unit 301 and the communication method deciding unit 303 of the video processor 30 illustrated in FIG. 3. The following description of the second embodiment will not thus describe in detail what is similar to that of the first embodiment, but differences from the first embodiment will be chiefly described.

3-1. DETAILS OF COMMUNICATION STATUS GRASPING PROCESS

The communication status grasping unit 301 illustrated in FIG. 3 detects the positions of objects (the antenna of the endoscope 10, the antennas of the relays 20a to 20c, and an obstacle (a member of the medical staff 501) in the example illustrated in FIG. 4) in an operating room on the basis of an operating room image in the second embodiment. At this time, the communication status grasping unit 301 also detects even the motion of the obstacle. The communication status grasping unit 301 detects a communication path on the basis of the position of the antenna of the video processor 30 provided in advance, and the detected position of the antenna of the endoscope 10 and the detected positions of the antennas of the relays 20*a* to 20*c*. The communication status grasping unit 301 then grasps the communication status of the communication path in accordance with whether the obstacle is in the communication path, even in light of the motion of the obstacle.

Figure 7:
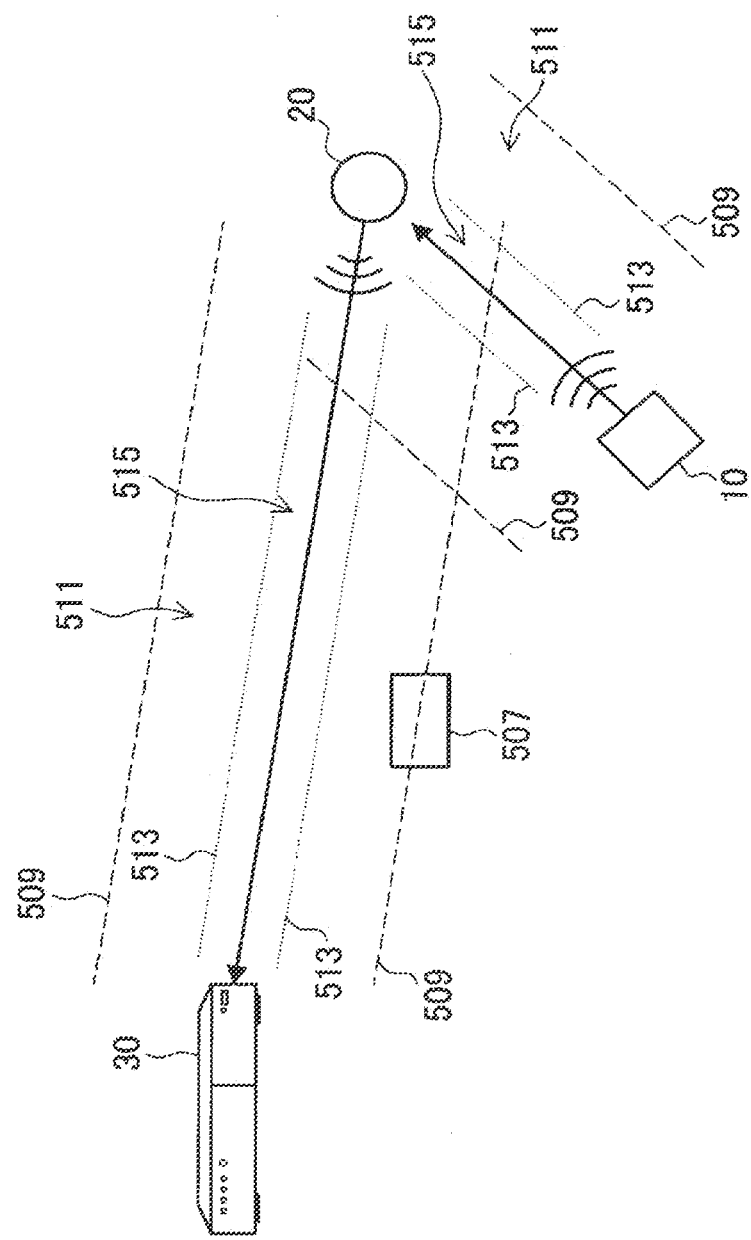
FIG. 7 is an explanatory diagram for describing a communication status grasping process executed by a communication status grasping unit in a second embodiment in more detail.

Here, the details of a communication status grasping process executed by the communication status grasping unit 301 in the second embodiment, such as a criterion for determining in accordance with the motion of an obstacle whether the obstacle is in a communication path, will be more specifically described with reference to FIG. 7. FIG. 7 is an explanatory diagram for describing the communication status grasping process executed by the communication status grasping unit 301 in the second embodiment in more detail.

FIG. 7 schematically illustrates the endoscope 10, the relay 20, and the video processor 30. FIG. 7 simulatively illustrates communication paths from the endoscope 10 to the video processor 30 via the relay 20 by solid arrows. Further, the Mayo table 507 is illustrated as an example of an obstacle in an operating room.

As illustrated in FIG. 7, a predetermined area including a communication path is set as alerting areas 511 in the second embodiment. The alerting areas 511 are similar to those set in the first embodiment. Here, in addition to the alerting areas 511, predetermined areas that include the communication paths and are narrower than the alerting areas 511 are set as risk areas 515 in the second embodiment. The risk area 515 is an area in which there is a high probability that the communication is blocked in a case where the area has an object therein, and the risk area 515 does not permit the presence of any object.

In the example illustrated in FIG. 7, the areas that are included in a predetermined distance from a substantially straight line connecting the antenna of the endoscope 10 to the antenna of the relay 20, and a substantially straight line connecting the antenna of the relay 20 to the antenna of the video processor 30, and are narrower than the alerting areas 511 are set as the risk areas 515. FIG. 7 illustrates risk lines 513 serving as the borders of the risk areas 515 by dashed lines that are different in type from the alerting lines 509.

The communication status grasping unit 301 illustrated in FIG. 3 detects the position of the antenna of the endoscope 10 and the position of the antenna of the relay 20 on the basis of an operating room image, and detects the position (spatial coordinates) of a communication path in an operating room on the basis of the position information thereof, the position information of the antenna of the video processor 30 input in advance in the second embodiment. The communication status grasping unit 301 then sets the alerting area 511 and the risk area 515 for the communication path. Further, the communication status grasping unit 301 detects the position (spatial coordinates) of the Mayo table 507 in the operating room on the basis of the operating room image.

When detecting the position of the Mayo table 507, the communication status grasping unit 301 also detects the motion of the Mayo table 507 in the second embodiment. The motion information of the Mayo table 507 detected by the communication status grasping unit 301 includes information indicating whether the Mayo table 507 stands still or is moving. Further, in a case where the Mayo table 507 is moving, the motion information may additionally include information on the moving direction or the moving speed. A variety of methods such as a method for acquiring the motion of an object in an image as a motion vector which are generally used in the field of image analysis processing can be used to detect the motion. The detailed description is not therefore made here.

In a case where an object is in the risk area 515, the communication status grasping unit 301 determines that the communication status in the communication path is not stable whether the object is a still object or a moving object. Further, in a case where a moving object is in the alerting area 511, the communication status grasping unit 301 also determines that the communication status in the communication path is not stable. Meanwhile, in a case where a still object is in the alerting area 511, but is not in the risk area 515, the communication status grasping unit 301 determines that the communication status in the communication path is stable. The communication method deciding unit 303 illustrated in FIG. 3 switches the wireless channel to another communication path having no object in the risk area 515, and having no moving object in the alerting area 511 on the basis of a result of the determination made by the communication status grasping unit 301.

Although the Mayo table 507 that is a still object is in the alerting area 511 of the communication path in the example illustrated in FIG. 7, the Mayo table 507 is not in the risk area 515. The communication status grasping unit 301 thus determines that the communication status is stable in the communication path. In this case, the communication method deciding unit 303 does not switch the wireless channel, but the communication using the current communication path continues.

In this way, the alerting area 511 and the risk area 515 are set for a communication path, the stability of the communication in the communication path is determined in accordance with the entry of an object to the alerting area 511 and/or the risk area 515 even in light of the motion of the object in the second embodiment. Thus, for example, in a case where the stability of communication is not hindered like a case where a still object is in an area that is the alerting area 511, but not the risk area 515, the communication path is not switched. According to the second embodiment, determining the stability of the communication in a communication path even in light of the motion of an object improves the accuracy of the determination, and makes it possible to secure more communication paths (i.e., candidates for switchable communication paths) that are determined to be stable. Further, a communication path is switched owing to the entry of a moving object to the alerting area 511. Accordingly, even in a case where an object that has stood still until then suddenly moves toward a communication path, the communication is not blocked, but it is possible to continuously perform stable communication.

The risk areas 515 may also be set as appropriate in accordance with the frequency band of radio waves used for wireless communication similarly to the alerting areas 511 described with reference to FIG. 5. The example illustrated in FIG. 7 assumes the use of millimeter waves, which have the stronger property of traveling straight. Accordingly, the risk areas 515 are set for substantially straight lines connecting the devices on the communication paths. For example, in a case where radio waves of a lower frequency band are used, the radio waves are predicted to diffuse more and propagate between the devices. The risk areas 515 may be therefore set, for example, as substantially conical areas that gradually increase in cross-sectional area from the antenna of the transmitting device to the antenna of the receiving device. In this way, in light of the frequency band or the like of radio waves used for wireless communication, the risk areas 515 can be set as areas that include an area in which the presence of an object can actually block the radio waves.

3-2. COMMUNICATION CONTROL METHOD

Figure 8:
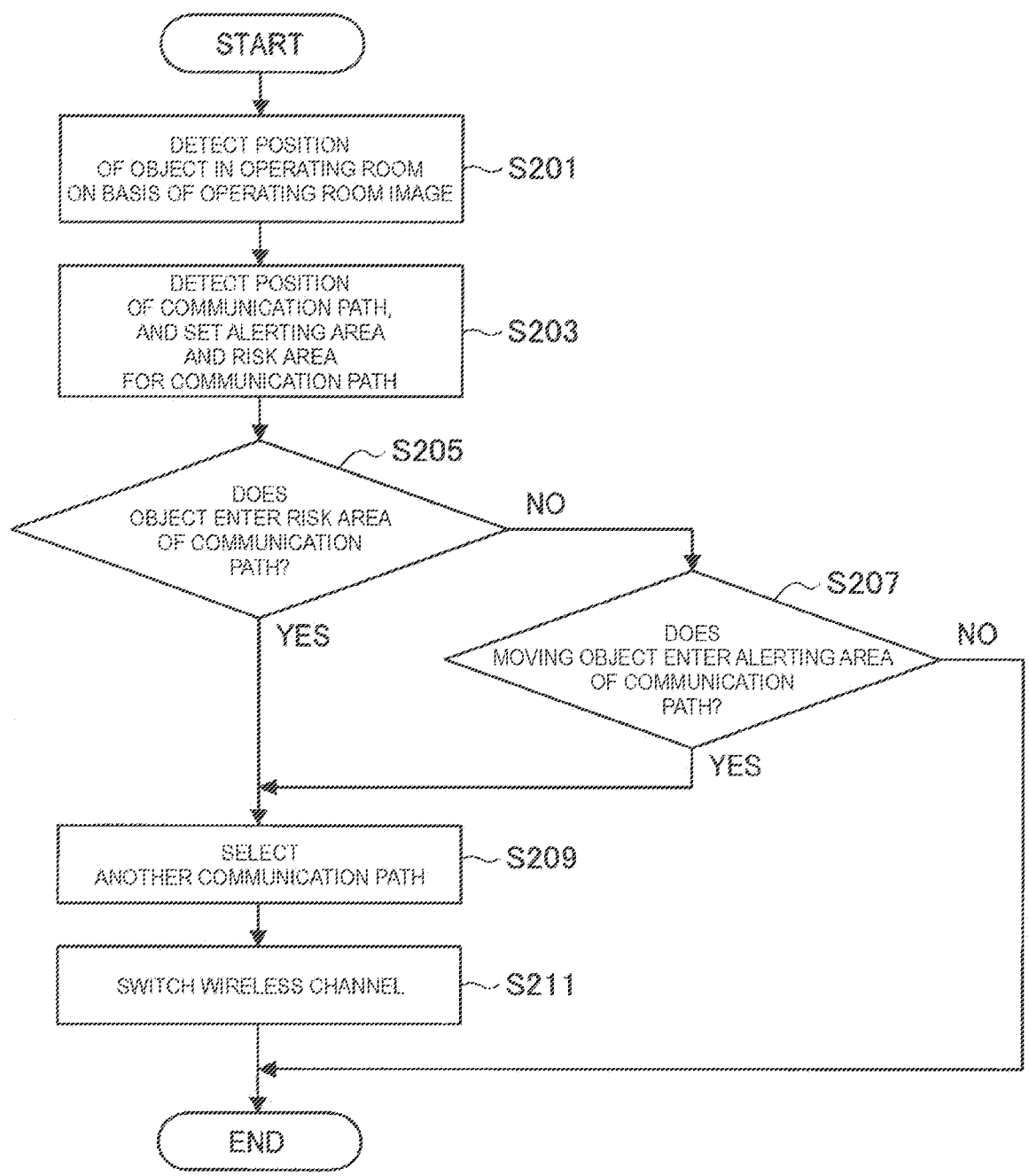
FIG. 8 is a flowchart illustrating an example of a processing procedure of a communication control method according to the second embodiment.

A processing procedure of a communication control method according to the second embodiment will be described with reference to FIG. 8. FIG. 8 is a flowchart illustrating an example of a processing procedure of a communication control method according to the second embodiment.

FIG. 8 illustrates that the position of an object in an operating room is first detected on the basis of an operating room image in the communication control method according to the second embodiment (step S201). Specifically, in step S201, the positions of the wireless input and output points (antennas) of respective devices that transmit surgical site image information from the endoscope 10 to the video processor 30, and the position of an object (such as the medical staff 501 or the Mayo table 507 illustrated in FIG. 2) that can obstruct the communication are at least detected. However, the positions of the antennas of all the devices do not have to be necessarily detected on the basis of the operating room image. The position information of the antennas of some of the devices such as the video processor 30 may also be input in advance as known data. Further, in step S201, the motion of the object that can obstruct the communication can also be detected.

Next, the position of a communication path is detected on the basis of the position of the object detected in step S201, and an alerting area and a risk area are set for the detected communication path (step S203). For example, in a case where millimeter waves are used for wireless communication, the communication path is detected as a substantially straight line connecting the antennas of the respective devices that transmit the surgical site image information from the endoscope 10 to the video processor 30, in light of the strong property of the millimeter waves to travel straight. Further, the alerting area is set as the area that is included in a predetermined distance from the line of the communication path, and the risk area is set as the area that is included in a predetermined distance from the line of the communication path and is narrower than the alerting area (see FIG. 7).

The second embodiment is not, however, limited to the example. The communication path may be detected on the basis of the positions of the antennas of the respective devices in light of the frequency band or the like of radio waves used for wireless communication. Further, the alerting areas include an area in which the presence of an object can actually block radio waves, and areas larger than the area can be set as the alerting areas 511. Further, the risk area can be set as an area in which the presence of an object can actually block radio waves.

Next, it is determined on the basis of the position of the object detected in step S201 and the alerting area set in step S203 whether the object is in the risk area of the communication path (step S205). Whether the object is a still object or a moving object, it is determined in step S205 whether the object is in the risk area.

In a case where it is not determined in step S205 that the object is in the risk area, the processes proceed to step S207. In step S207, it is determined on the basis of the position and motion of the object detected in step S201, and the alerting area set in step S203 whether the moving object is in the alerting area of the communication path.

In a case where it is not determined in step S207 that the moving object is in the alerting area, the series of processes according to the communication control method ends with no particular processes, and the transmission of surgical site image information continues in the communication path. This is because the stability of the communication in the communication path is considered strong in this case since no object is in the risk area of the communication path, and no moving object is in the alerting area.

Meanwhile, in a case where it is determined in step S205 that the object is in the risk area, or in a case where it is determined in step S207 that the moving object is in the alerting area, the processes proceed to step S209.

The respective processes shown in step S201 to step S207 correspond to, for example, processes performed by the communication status grasping unit 301 illustrated in FIG. 3.

In step S209, another communication path is selected that is different from the communication path having the object in the risk area or the communication path having the moving object in the alerting area. A communication path that has no object in the risk area, has no moving object in the alerting area, and allows for more stable communication is selected as the other communication path from the communication paths detected in step S203. The wireless channel is then switched to the wireless channel corresponding to the communication path selected in step S209 (step S211). This switches the wireless channel from the communication path having the risk that an object enters the risk area or a moving object enters the alerting area and interrupts the communication to a communication path that allows for more stable communication. It is thus possible to transmit the surgical site image information to the video processor 30 without the surgical site image information breaking off.

The respective processes shown in step S209 and step S211 correspond to, for example, processes performed by the communication method deciding unit 303 illustrated in FIG. 3.

The processing procedure of the communication control method according to the second embodiment has been described above with reference to FIG. 8. The series of processes illustrated in FIG. 8 is repeatedly executed at predetermined intervals in the second embodiment. A stable surgical site image is thus always displayed.

4. MODIFICATIONS

Some modifications of the above-described first and second embodiments will be described. Additionally, the above-described first and second embodiments, and each of the following modifications may be combined to the extent possible for realization.

4-1. MODIFICATION OF DECISION PROCESS OF COMMUNICATION METHOD

The communication method deciding unit 303 illustrated in FIG. 3 performs a process of switching a communication path to a communication path that allows for more stable communication in the above-described first and second embodiments. The process of switching communication paths is, however, an example of a decision process of a communication method. The decision process of a communication method performed by the communication method deciding unit 303 is not limited to the example. For example, the communication method deciding unit 303 may decide the frequency band of radio waves used for the wireless communication between the endoscope 10 and the video processor 30 as a communication method.

As described above in (2-1. Configuration of Communication Control System), millimeter waves are favorably used for the wireless communication between the endoscope 10 and the video processor 30 in a manner that surgical site image information having a large amount of data can be transmitted fast in the first and second embodiments. Millimeter waves, however, has the relatively strong property of traveling straight because of its high frequency band. Thus, if there is an obstacle on the straight line connecting the antennas of devices on a communication path, there is a higher probability that the transmission and reception of radio waves are interfered with.

Therefore, in the present modification, in a case where it is determined that the stability of the communication in the currently used communication path is weak, the communication method deciding unit 303 switches the communication standard of the wireless communication between the endoscope 10 and the video processor 30 and changes the frequency band of radio waves used for the wireless communication, for example, to a lower frequency band of some GHz.

A variety of known communication standards may be used for the standard of wireless communication that uses radio waves of a lower frequency band. For example, Miracast (registered trademark), WiDi (registered trademark), AirPlay (registered trademark), a variety of communication standards that use the ultra wide band (UWB) scheme, WHDI (registered trademark), or the like can be used for wireless communication for transferring image information with a lower frequency band. Further, not limited to the transfer use of image information, what complies with the respective standards such as IEEE 802.11b/a/g/j/n/ac, TransferJet (registered trademark), or the like may be used for wireless communication that uses radio waves of a lower frequency band.

Radio waves having a lower frequency band have the weaker property of traveling straight than that of millimeter waves. Accordingly, even in a case where there is an obstacle on the line between the antennas of devices on a communication path, the radio waves can propagate between the antennas by diffracting around the obstacle. More stable communication can be thus realized. Even in a case where radio waves having a low frequency band are used like the present modification, the stability of the communication in a communication path may be determined in accordance with the entry of an object to an alerting area or a risk area similarly to the above-described first or second embodiment.

In this way, according to the present modification, for example, in a case where it is determined that there is an obstacle on a communication path, and it is difficult for wireless communication using millimeter waves to assure stable communication, the communication standard used for the wireless communication is changed in a manner that wireless communication using radio waves of a lower frequency band, which have the weaker property of traveling straight, is performed. Thus, even in a case where there is an obstacle on a communication path, it is possible to more stably perform communication.

However, in a case where radio waves of a low frequency band are used, it can be difficult to perform fast communication for a high-resolution image. Thus, in a case where the communication standard is switched in a manner that radio waves of a lower frequency band are used, image processing for making the resolution of the surgical site image lower may be performed as appropriate to reduce the amount of data so as to cause no delay during communication before the surgical site image information is transmitted from the endoscope 10.

Additionally, the processes performed by the communication method deciding unit 303 according to the present modification may be executed instead of the processes performed by the communication method deciding unit 303 according to the above-described first or second embodiment, or in combination with the processes performed by the communication method deciding unit 303 according to the above-described first or second embodiment. That is, in a case where it is determined that the stability of the communication in the currently used communication path is weak, the frequency band of the radio waves alone may be changed, or the communication path may be switched to a more stable communication path having no obstacle thereon and the frequency band of the radio waves may be changed.

4-2. MODIFICATION OF POSITION FOR DISPOSING OPERATING ROOM CAMERA

The operating room camera 40 is installed at a position such as the ceiling of an operating room at which the operating room camera 40 looks down on the operating room as illustrated in FIG. 2 in the above-described first and second embodiments. The position for disposing the operating room camera 40 is not, however, limited to the example. The operating room camera 40 may be disposed at any position as long as the antenna of the endoscope 10 and the antenna of the relay 20 are included at least within the image capturing range.

For example, the operating room camera 40 may also be provided to each relay 20 instead of the operating room camera 40 provided at a position at which the operating room camera 40 looks down on the operating room, or in combination with the operating room camera 40 provided at a position at which the operating room camera 40 looks down on the operating room. In this case, the operating room camera 40 can be installed in each relay 20 to include, within the image capturing range, the endoscope 10 and the relay 20 other than the relay 20 in which the operating room camera 40 itself is installed.

The communication status grasping unit 301 illustrated in FIG. 3 can detect, from an operating room image from the certain operating room camera 40, the position of the antenna of the endoscope 10, the position of the antenna of another one of the relays 20, and the position of an obstacle as the relative positions from the operating room camera 40. The relative position of an object from each relay 20 in the operating room can be detected on the basis of an operating room image from each operating room camera 40 provided to each relay 20. Accordingly, the communication status grasping unit 301 can detect the position of the antenna of the endoscope 10, the positions of the antennas of the relays 20, and the position of the obstacle as the absolute spatial coordinates by integrating the detected position information. The communication status grasping unit 301 can thus grasp the communication status of each communication path similarly to a case where the operating room camera 40 is installed at a position at which the operating room camera 40 looks down on an operating room.

4-3. NOTIFICATION OF COMMUNICATION PATH

The communication control system 1 according to the above-described first and second embodiments may further has a function of notifying a medical staff in an operating room of information on the grasped communication status between the endoscope 10 and the video processor 30 by the communication status grasping unit 301. For example, the video processor 30 can have this notification function of the notification unit. The notification unit may notify a medical staff, for example, of the currently used communication path as the communication status. Further, the notification unit may notify a medical staff of, for example, each communication path in an operating room as the communication status. On the basis of the information of which the medical staff is notified, the medical staff can pay attention to the motion or the disposition of instruments, for example, in a manner that all the communication paths are not blocked.

For example, the relay 20 may include a lamp such as a light emitting diode (LED) as a means of notifying a medical staff of the currently used communication path, and the notification unit may perform control to turn on the lamp of the relay 20 currently functioning as the communication path. Further, for example, a display device such as a monitor may be additionally provided in an operating room to indicate the status of a communication path, and the notification unit may display a line or the like indicating the currently used communication path on the display unit along with a sketch of the operating room. Further, for example, to notify a medical staff of each communication path in an operating room, the notification unit may display a line or the like indicating another communication path on the display device for indicating the status of the communication path along with a line indicating the currently used communication path.

5. SUPPLEMENTAL INFORMATION

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

1

A communication control device including:
a communication status grasping unit configured to grasp a communication status of wireless communication of image information between an image shooting device and a surgical site image information acquiring unit on the basis of an operating room image showing a situation of an operating room, the image shooting device capturing an image of a surgical site of a patient, the surgical site image information acquiring unit acquiring information on a surgical site image captured by the image shooting device for display control of the surgical site image; and
a communication method deciding unit configured to decide a communication method between the image shooting device and the surgical site image information acquiring unit on the basis of the grasped communication status.

2

The communication control device according to (1), wherein
the communication status grasping unit grasps stability of communication in communication paths between the image shooting device and the surgical site image information acquiring unit as the communication status, and
the communication method deciding unit selects, as the communication method, a communication path that allows for more stable communication from the communication paths.

3

The communication control device according to (2), wherein
the communication status grasping unit grasps a status of the communication path by detecting, on the basis of the operating room image, positions of antennas that form the communication path, and a position of an obstacle that obstructs transmission and reception of a radio wave between the antennas.

4

The communication control device according to (3),
the communication paths exist between the image shooting device and the surgical site image information acquiring unit, the communication paths including the communication path that passes through a relay and the communication path that does not pass through the relay, the relay relaying the wireless communication between the image shooting device and the surgical site image information acquiring unit, and
the communication status grasping unit at least detects a position of an antenna of the image shooting device and a position of an antenna of the relay as the positions of the antennas on the basis of the operating room image, the antennas forming the communication path.

5

The communication control device according to any one of (2) to (4), wherein
the communication status grasping unit detects that an obstacle that obstructs the communication between the image shooting device and the surgical site image information acquiring unit enters a first area including the communication path, and
the communication method deciding unit selects, as the communication path that allows for more stable communication, the communication path other than the communication path that the obstacle enters.

6

The communication control device according to (5), wherein
the communication status grasping unit detects that the obstacle enters at least one of the first area and a second area that includes the communication path and is narrower than the first area, and
in a case where the obstacle that is a still object or a moving object enters the second area, or in a case where the obstacle that is the moving object enters the first area, the communication method deciding unit selects, as the communication path that allows for more stable communication, the communication path other than the communication path that the obstacle enters.

7

The communication control device according to any one of (2) to (6), wherein
a millimeter wave is used for the wireless communication between the image shooting device and the surgical site image information acquiring unit, and
the communication path is a substantially straight path connecting antennas that transmit and receive the millimeter wave.

8

The communication control device according to any one of (1) to (7), wherein
the operating room image is acquired by an operating room camera provided at a position at which the operating room camera looks down on the operating room.

9

The communication control device according to any one of (1) to (7), wherein
the operating room image is acquired by an operating room camera provided to a relay that relays the wireless communication between the image shooting device and the surgical site image information acquiring unit.

10

The communication control device according to any one of (1) to (9), wherein
the communication status grasping unit grasps stability of communication in a communication path between the image shooting device and the surgical site image information acquiring unit as the communication status, and
the communication method deciding unit changes, as the communication method, a frequency band of a radio wave used for the wireless communication between the image shooting device and the surgical site image information acquiring unit to a frequency band that allows for more stable communication.

11

The communication control device according to (10), wherein
the communication method deciding unit selects a frequency band lower than a millimeter wave band as the frequency band that allows for more stable communication.

12

The communication control device according to any one of (1) to (11), wherein
the image shooting device is an endoscope.

13

The communication control device according to any one of (1) to (12), further including:
a notification unit configured to notify a user of the communication status of the wireless communication between the image shooting device and the surgical site image information acquiring unit.

14

A communication control method including, by a processor:
grasping a communication status of wireless communication of image information between an image shooting device and a surgical site image information acquiring unit on the basis of an operating room image showing a situation of an operating room, the image shooting device capturing an image of a surgical site of a patient, the surgical site image information acquiring unit acquiring information on a surgical site image captured by the image shooting device for display control of the surgical site image; and
deciding a communication method between the image shooting device and the surgical site image information acquiring unit on the basis of the grasped communication status.

15

A program for causing a processor of a computer to execute:
a function of grasping a communication status of wireless communication of image information between an image shooting device and a surgical site image information acquiring unit on the basis of an operating room image showing a situation of an operating room, the image shooting device capturing an image of a surgical site of a patient, the surgical site image information acquiring unit acquiring information on a surgical site image captured by the image shooting device for display control of the surgical site image; and
a function of deciding a communication method between the image shooting device and the surgical site image information acquiring unit on the basis of the grasped communication status.

16

A communication control system including:
an operating room camera configured to capture an operating room image showing a situation of an operating room;
an image shooting device configured to capture an image of a surgical site of a patient; and
a communication control device including a surgical site image information acquiring unit configured to acquire information on a surgical site image captured by the image shooting device for display control of the surgical site image, a communication status grasping unit configured to grasp a communication status of wireless communication of image information between the image shooting device and the surgical site image information acquiring unit on the basis of the operating room image, and a communication method deciding unit configured to decide a communication method between the image shooting device and the surgical site image information acquiring unit on the basis of the grasped communication status.

REFERENCE SIGNS LIST 1 communication control system
10 endoscope (image shooting device)
20 relay
30 video processor (display control device, communication control device)
40 operating room camera
101 surgical site image information transmitting unit
201 surgical site image information transmitting and receiving unit
301 operating room image information transmitting unit
303 communication status grasping unit
305 communication method deciding unit
401 operating room image information acquiring unit
511 alerting area
515 risk area

The invention claimed is:

1. A communication control device, comprising:
processing circuitry configured to
obtain position information indicating a position of a transmitter, a receiver and objects in a space, wherein the objects include at least one human,
select a first communication path between the transmitter and the receiver of a plurality of wireless communication paths based on the position information so that wireless communication is stable between the transmitter and the receiver,
switch, based on a communication status of the first communication path, a millimeter wave band to a lower frequency wave band than the millimeter wave,
wherein the transmitter wirelessly transmits an image captured by a device coupled to the transmitter or to the receiver,
wherein the processing circuitry is further configured to perform processing to reduce an amount of data of the image when the lower frequency wave band is used, and
wherein the processing circuitry is further configured to obtain moving information indicating a moving of the objects and select a first communication path between the transmitter and the receiver of the plurality of wireless communication paths based on the position information and the moving information.

2. The communication control device according to claim 1, wherein the objects include at least one of stands or devices in the space.

3. The communication control device according to claim 1, wherein the processing circuitry is further configured to switch the first communication path to a second communication path when the objects are present between the receiver and the transmitter.

4. The communication control device according to claim 1, wherein the processing circuitry is further configured to
determine whether an area defined based on the position of the transmitter and the receiver include the objects, and
switch the first communication path to a second communication path when the objects are present in the area.

5. The communication control device according to claim 4, wherein the processing circuitry is further configured to determine whether the objects are present in the area based on a sensing data of the space.

6. The communication control device according to claim 5, wherein the processing circuitry is further configured to determine whether the objects are present in the area based on imaging data of the space.

7. The communication control device according to claim 6, wherein the imaging data is captured by a room camera.

8. The communication control device according to claim 5, wherein the processing circuitry is further configured to determine whether the objects are an obstacle for the wireless communication based on the sensing data.

9. The communication control device to claim 1, wherein the processing circuitry is further configured to control a display to display a room map and a communication path used for connection between the transmitter and the receiver.

10. The communication control device to claim 1, wherein the processing circuitry is further configured to control a repeater, used for connection between the transmitter and the receiver, to turn on a lamp of the repeater.

11. The communication control device according to claim 1, wherein the image is an endoscope image captured by an endoscope system.

12. A communication control method performed by processing circuitry of a communication control device, the method comprising:
obtaining position information indicating a position of a transmitter, a receiver and objects in a space, wherein the objects include at least one human,
selecting a first communication path between the transmitter and the receiver of a plurality of wireless communication paths based on the position information so that wireless communication is stable between the transmitter and the receiver,
switching, based on a communication status of the first communication path, a millimeter wave band to a lower frequency wave band than the millimeter wave,
wherein the transmitter wirelessly transmits an image captured by a device coupled to the transmitter or to the receiver,
performing, by the communication control device, processing to reduce an amount of data of the image when the lower frequency wave band is used, and
obtaining moving information indicating a moving of the objects and selecting a first communication path between the transmitter and the receiver of the plurality of wireless communication paths based on the position information and the moving information.

13. A communication control system comprising:
a device including processing circuitry configured to:
obtain position information indicating a position of a transmitter, a receiver and objects in a space, wherein the objects include at least one human,
select a first communication path between the transmitter and the receiver of a plurality of wireless communication paths based on the position information so that wireless communication is stable between the transmitter and the receiver,
switch, based on a communication status of the first communication path, a millimeter wave band to a lower frequency wave band than the millimeter wave,
wherein the transmitter wirelessly transmits an image captured by a device coupled to the transmitter or to the receiver,
wherein the processing circuitry is further configured to perform processing to reduce an amount of data of the image when the lower frequency wave band is used, and
wherein the processing circuitry is further configured to obtain moving information indicating a moving of the objects and select a first communication path between the transmitter and the receiver of the plurality of wireless communication paths based on the position information and the moving information.

14. The communication control system according to claim 13, wherein the device is a medical device.

15. The communication control system according to claim 13, wherein the space is a surgical room.

16. The communication control system according to claim 13, wherein the objects include at least one of stands or devices in the space.

17. The communication control system according to claim 13, wherein the processing circuitry is further configured to switch the first communication path to a second communication path when the objects are present between the receiver and the transmitter.

* * * * *